(12) United States Patent
Moore et al.

(10) Patent No.: US 8,957,113 B2
(45) Date of Patent: *Feb. 17, 2015

(54) TRANEXAMIC ACID FORMULATIONS

(75) Inventors: Keith A. Moore, Loveland, OH (US); Ralph A. Heasley, Webster Grove, MN (US); Jeffrey S. Greiwe, Ft. Thomas, KY (US); John W. Facemire, Douglasville, GA (US); Jason D. Modest, Minneapolis, MN (US)

(73) Assignee: Ferring B.V., Hoofddorp (NL)

( * ) Notice: Subject to any disclaimer, the term of this patent is extended or adjusted under 35 U.S.C. 154(b) by 132 days.

This patent is subject to a terminal disclaimer.

(21) Appl. No.: 13/016,800

(22) Filed: Jan. 28, 2011

(65) Prior Publication Data

US 2011/0230559 A1 Sep. 22, 2011

Related U.S. Application Data

(63) Continuation of application No. 12/433,408, filed on Apr. 30, 2009, now abandoned, which is a continuation-in-part of application No. 12/220,241, filed on Jul. 23, 2008, now abandoned, which is a continuation of application No. 11/072,162, filed on Mar. 4, 2005, now abandoned.

(60) Provisional application No. 60/550,113, filed on Mar. 4, 2004, provisional application No. 60/592,885, filed on Jul. 30, 2004.

(51) Int. Cl.
| | | |
|---|---|---|
| A61K 31/19 | (2006.01) | |
| A61K 31/195 | (2006.01) | |
| A61K 9/20 | (2006.01) | |
| A61K 9/28 | (2006.01) | |

(52) U.S. Cl.
CPC ............. *A61K 31/195* (2013.01); *A61K 9/2009* (2013.01); *A61K 9/2027* (2013.01); *A61K 9/2054* (2013.01); *A61K 9/2059* (2013.01); *A61K 9/2846* (2013.01); *A61K 9/2866* (2013.01)
USPC ........................................................ 514/574

(58) Field of Classification Search
CPC .......................... C07C 2101/14; A61K 31/195
USPC ........................................................ 514/574
See application file for complete search history.

(56) References Cited

U.S. PATENT DOCUMENTS

| | | | |
|---|---|---|---|
| 3,870,790 | A | 3/1975 | Lowrey et al. |
| 4,171,377 | A | 10/1979 | Green et al. |
| 4,258,030 | A | 3/1981 | Sasaki et al. |
| 4,389,393 | A | 6/1983 | Schor et al. |
| 4,465,662 | A | 8/1984 | Sato et al. |
| 4,483,867 | A | 11/1984 | Svahn et al. |
| 4,711,782 | A | 12/1987 | Okada |
| 5,068,110 | A | 11/1991 | Fawzi et al. |
| 5,229,135 | A | 7/1993 | Philipon et al. |
| 5,242,337 | A | 9/1993 | Greenwood et al. |
| 5,271,945 | A | 12/1993 | Yoshioka |
| 5,506,264 | A | 4/1996 | Fujimura et al. |
| 5,575,987 | A | 11/1996 | Kamei et al. |
| 5,622,657 | A | 4/1997 | Takada et al. |
| 5,650,174 | A | 7/1997 | Muhammad et al. |
| 5,723,269 | A | 3/1998 | Akagi et al. |
| 5,738,874 | A | 4/1998 | Conte et al. |
| 5,747,030 | A | 5/1998 | Kohnert et al. |
| 5,807,583 | A | 9/1998 | Kristensen et al. |
| 5,858,411 | A | 1/1999 | Nakagami et al. |
| 5,874,463 | A | 2/1999 | Ancira |
| 5,877,175 | A | 3/1999 | Sargent et al. |
| 5,897,910 | A | 4/1999 | Rosenberg |
| 6,051,253 | A | 4/2000 | Zettler |
| 6,056,977 | A | 5/2000 | Bhagwat et al. |
| 6,066,339 | A | 5/2000 | Stark et al. |
| 6,113,943 | A | 9/2000 | Okada et al. |
| 6,120,802 | A | 9/2000 | Breitenbach |
| 6,159,502 | A | 12/2000 | Jones |
| 6,197,331 | B1 | 3/2001 | Lerner et al. |
| 6,274,171 | B1 | 8/2001 | Sherman et al. |
| 6,300,369 | B1 | 10/2001 | Ancira |
| 6,328,979 | B1 | 12/2001 | Ywmashita |
| 6,433,215 | B1 | 8/2002 | Jung |
| 6,548,084 | B2 | 4/2003 | Leonard et al. |
| 6,551,616 | B1 | 4/2003 | Notario et al. |
| 7,192,608 | B2 | 3/2007 | Ochiai |
| 7,235,530 | B2 | 6/2007 | Blair et al. |
| 7,273,624 | B2 | 9/2007 | Rosenberg et al. |
| 7,351,740 | B2 | 4/2008 | Zerangue |
| 7,947,739 | B2 | 5/2011 | Moore et al. |
| 8,022,106 | B2 | 9/2011 | Moore et al. |
| 8,273,795 | B2 | 9/2012 | Moore et al. |
| 8,487,005 | B2 | 7/2013 | Moore et al. |

(Continued)

FOREIGN PATENT DOCUMENTS

| | | |
|---|---|---|
| CA | 2086565 | 7/1994 |
| EP | 0 998 916 | 5/2000 |

(Continued)

OTHER PUBLICATIONS

Cyklokapron (Package Insert, Pharmacia and Upjohn. 6pgs. 2000).*
1996 Physician's Desk Reference, 50th Edition, on Tranexamic acid (Cyklokapron), pp. 1950-1951.
A brochure containing information relating to Tab. Trexamic and Tab. Trexamic-M (Reference A14), submitted to USPTO on Jul. 6, 2010.
Abbott, J.A., et al. "Quality of Life should Be Considered the Primary outcome for Measuring success of endometrial Ablation", *J. Am. Assoc. Gynecol. Laparosc.*, 2003, 10(4); 491-495.
ACOG Practice Bulletin; "Management of anovulatory bleeding, 2000, No. 14", *Int. J. Gynecol. Obstetrics* 72(2001) 263-271.
Advisory Action dated Oct. 23, 2007 for U.S. Appl. No. 10/631,371, 3 pgs.
Advisory Action dated Jun. 13, 2011 for U.S. Appl. No. 11/346,710, 3 pgs.
Advisory Action dated Dec. 12, 2011 for U.S. Appl. No. 12/228,489, 5 pgs.
Alexander, D.A. et al, "Randomized trial comparing hysterectomy with endometrial ablation of dysfunctional bleeding; psychiatric and psychosocial aspects," *Brit. Med. J.*, 1996, 312:280-284.
Andersch, Bjorn et al, "An Objective Evaluation of Flurbiprofen and Tranexamic Acid in the Treatment of Idiopathic Menorrhagia," *Acta Obstet. Gynecol. Scand.*, 1988; 67: 645-648.
Anderson L., et al, "Special Considerations with Regard to the Dosage of Tranexamic Acid in patients with Chronic Renal Diseases," *Urological Research* 6, 83-88 (1978).

(Continued)

*Primary Examiner* — Wu-Cheng Winston Shen
*Assistant Examiner* — Christopher R Stone
(74) *Attorney, Agent, or Firm* — Fish & Richardson P.C.

(57) ABSTRACT

Disclosed are immediate release oral tranexamic acid formulations and methods of treatment therewith.

30 Claims, 6 Drawing Sheets

(56) References Cited

U.S. PATENT DOCUMENTS

| | | | |
|---|---|---|---|
| 8,791,160 | B2 | 7/2014 | Moore et al. |
| 8,809,394 | B2 | 8/2014 | Moore et al. |
| 2002/0132855 | A1 | 9/2002 | Nelson et al. |
| 2003/0133985 | A1 | 7/2003 | Louie-Helm et al. |
| 2003/0190353 | A1 | 10/2003 | Oosterbaan et al. |
| 2004/0006021 | A1 | 1/2004 | Rojkjaer et al. |
| 2004/0052843 | A1 | 3/2004 | Lerner et al. |
| 2004/0096499 | A1 | 5/2004 | Vaya |
| 2004/0258753 | A1 | 12/2004 | Demeesteer |
| 2005/0025825 | A1 | 2/2005 | Heasley et al. |
| 2005/0059742 | A1 | 3/2005 | Jarbour et al. |
| 2005/0244495 | A1 | 11/2005 | Moore et al. |
| 2005/0245614 | A1 | 11/2005 | Moore et al. |
| 2005/0267014 | A1 | 12/2005 | Rojkaer et al. |
| 2006/0003006 | A1 | 1/2006 | Remon |
| 2006/0018933 | A1 | 1/2006 | Vaya et al. |
| 2006/0018934 | A1 | 1/2006 | Vaya |
| 2006/0127476 | A1 | 6/2006 | Heasley et al. |
| 2006/0193914 | A1 | 8/2006 | Asworth |
| 2006/0287258 | A1 | 12/2006 | Jabbour et al. |
| 2007/0020335 | A1 | 1/2007 | Chen et al. |
| 2007/0027210 | A1 | 2/2007 | Zerangue et al. |
| 2008/0193414 | A1 | 8/2008 | Proudfoot |
| 2008/0280981 | A1 | 11/2008 | Moore et al. |
| 2009/0017114 | A1 | 1/2009 | Moore et al. |
| 2009/0048341 | A1 | 2/2009 | Moore et al. |
| 2009/0209646 | A1 | 8/2009 | Moore et al. |
| 2009/0214644 | A1 | 8/2009 | Heasley et al. |
| 2009/0215898 | A1 | 8/2009 | Moore et al. |
| 2010/0143468 | A1 | 6/2010 | Moore et al. |
| 2010/0280117 | A1 | 11/2010 | Patrick et al. |
| 2012/0122985 | A1 | 5/2012 | Moore et al. |
| 2013/0012584 | A1 | 1/2013 | Moore et al. |
| 2013/0018100 | A1 | 1/2013 | Moore et al. |
| 2013/0096198 | A1 | 4/2013 | Moore et al. |

FOREIGN PATENT DOCUMENTS

| | | |
|---|---|---|
| EP | 0 923 934 | 8/2003 |
| EP | 1 586 315 | 10/2005 |
| GB | 2073019 | 10/1981 |
| JP | 57059847 | 4/1982 |
| JP | 4-243825 | 8/1992 |
| JP | 06-219942 | 8/1994 |
| JP | 7206660 | 8/1995 |
| JP | 9077726 | 3/1997 |
| JP | 9124878 | 5/1997 |
| JP | 9255542 | 9/1997 |
| JP | 10-017497 | 1/1998 |
| JP | 2000-159674 | 6/2000 |
| JP | 2001-163774 | 6/2001 |
| JP | 2002-265358 | 9/2002 |
| WO | WO 94/15904 | 7/1994 |
| WO | WO 96/19200 | 6/1996 |
| WO | WO 2004/028503 | 4/2004 |
| WO | WO 2004/060364 | 7/2004 |
| WO | WO 2005/011650 | 2/2005 |
| WO | WO 2006/023000 | 3/2006 |
| WO | WO 2006/023001 | 3/2006 |
| WO | WO 2008/111096 | 9/2008 |
| WO | WO 2008/148798 | 12/2008 |

OTHER PUBLICATIONS

Anderson, I. et al, "Role of Urokinase and Tissue Activator in Sustaining Bleeding and the Management Thereof with EACA and AMCA," *Annals N.Y. Acad. Sci.*, 146, p. 642-658. (1968).

Ansari, Tariq Mahmood, et al, "Spectrophotometric Determination of Tranexamic Acid in Pharmaceutical Bulk and Dosage Forms", Analytical Sciences, Sep. 2005, vol. 21, p. 1133-1135.

Apgar, Barbara S. et al, "Treatment of Menorrhagia", American Family Physician, Jun. 15, 2007, vol. 75, No. 12, p. 1813-1819.

Applicant's Accelerated Examination Support Document filed Feb. 26, 2010, U.S. Appl. No. 12/714,181, 6 pgs.

Applicant's Pre-examination Search Statement filed Feb. 26, 2010, U.S. Appl. No. 12/714,181, 6 pgs.

Applicant's Response to Final Office Action dated Jun. 14, 2007, filed Oct. 4, 2007, U.S. Appl. No. 10/631,371.

Applicant's Response to non-final Office Action dated Dec. 15, 2006, filed Mar. 13, 2007, U.S. Appl. No. 10/631,371, 9 pgs.

Applicant's Amendment in Reply to Action filed May 9, 2011, U.S. Appl. No. 12/228,489, 18 pages.

Applicant's Reply to Final Office Action filed Nov. 9, 2011, U.S. Appl. No. 12/228,489, 13 pages.

Article: "Health-Related Quality of Life and Activity limitation-Eight States", 1995, MMWR, 1998, 47(7), 134-140.

Astedt, B., "Clinical Pharmacology of Tranexamic Acid", *Scand. J. Gastroenterol.* 1987, 22 (suppl. 137), 22-25.

Attorney B. Jefferson Boggs et al., Watson Laboratories, Inc., Florida's Initial Disclosure of Non-Infringement, Invalidity and Unenforceability Contentions to Ferring B.V., pp. 1 and 7-15, dated Jan. 5, 2012.

Attorney B. Neighbarger et al., First Amended Answer, Affirmative Defenses and Counter-claims to Complaint for Patent Infringement, Case No. 11-cv-00481-RCJ-VPC, D. Nev., 8 pgs., dated Feb. 28, 2012.

Attorney B. Neighbarger et al., Second Amended Answer, Affirmative Defenses and Counter-claims to Complaint for Patent Infringement, Case No. 11-cv-00481-RCJ-VPC, D. Nev., 9 pgs., dated Mar. 12, 2012.

Attorney Kevin W. McCabe, Notice Letter Regarding Paragraph IV Certification Against U.S. Patent No. 7947739 to Tranexamic Acid Formulations Pursuant to Section 505(j)(2)(B)(ii) of the Federal Food, Drug, and Cosmetic Act, dated May 27, 2011 (11 pages).

Attorney Kevin W. McCabe, Notice Letter Regarding Paragraph IV Certification Against U.S. Patent No. 8022106 to Tranexamic Acid Formulations Pursuant to Section 505(j)(2)(B)(ii) of the Federal Food, Drug, and Cosmetic Act, dated Oct. 12, 2011 (10 pages).

Attorney M. Rounds et al., First Amended Answer, Affirmative Defenses and Counter-claims to Complaint for Patent Infringement, Case No. 11-cv-004810RCJ-VPC, D. Nev., 16 pgs., dated Feb. 28, 2012.

Attorney Michael D. Rounds et al., Watson's Points and Authorities in Opposition to Ferring's Motion to Dismiss Watsons's Amended Second Counterclaims for Invalidity, Case No. 11-cv-00481-RCJ-VPC, D. Nev., 123 pgs., dated Apr. 2, 2012.

Aulton et al. Pharmaceutics the Science of Dosage and Design, Chapters 1 (pp. 1-11), 5 (pp. 62-80) and 18 (pp. 304-321) (1988).

Bekassy, Z. et al., "Treatment with the Fibrinolytic Inhibitor Tranexamic Acid—Risk for Thrombosis?" *Acta Obstet. Gynecol. Scand.*, 1990; 69: 353-354.

Ben-Tovim, D.I., et al., "The Influence of Age and Weight on Women's Body Attitudes as measured by the Body Attitudes Questionnaire (BAQ)" j. Psychosomatic Res., 1994, 38(5) 477-481.

Berntorp, "No increased Risk of Venous Thrombosis in Women Taking Tranexamic Acid," *Thromb. Haemostat.*, 2001; 86: 714-5.

Bonnar J. et al., "Treatment of Menorrhagia during menstruation: randomized controlled trial of ethamsylate, mefenamic acid, and tranexamic acid," *Brit. Med. J.* 1996; 313: 579-82.

Bradshaw et al., Answer to Complaint for Patent Infringement and Counterclaims, dated Feb. 15, 2013, 16 pg.

Bravo et al., "In-Vitro Studies of Diclofenac Sodium Controlled-release Biopolymeric Hydrophilic Matrices", *J. Pharm. Pharmaceut. Sci.* 5(3), p. 213-219, 2002.

British National Formulary, ed., Section 2.11 Antifibrinolytic drugs and Haemostatics, p123, submitted to USPTO on May 6, 2010.

Busija, L. et al, "Magnitude and meaningfulness of change in SF-36 scores in four types of orthopedic surgery", Health and Quality of Life Outcomes, 2008, 6:55.

Callendar S., et al, "Treatment of Menorrhagia with Tranexamic Acid. A Double-blind Trial" *Brit. Med. J.*, 1970, 4, 214-216.

Cameron, Medical Management of Menorrhagia, *Current Obstetrics and Gynecology*, 1992, 2, 136-140.

Carlson, K. J., et al, "The Maine Women's health Study: I. Outcomes of hysterectomy", *Obstet. Gynecol.*, 1994; 83:556-65.

CECMED Product Characteristics; Rottapharms S.L.; solution for injection, IV, IV Infusion, oral, 5mg/ml. vial Aug. 18, 2009, 8 pgs.

(56) References Cited

OTHER PUBLICATIONS

Cella, D., May Clinic Proc. vol. 77(4), Apr. 2002, 384-392.
Chauhan, Cynthia, "Denouement: A Patient-Reported Observation," *Value in Health*, 2007: 10: suppl 2, 1098-3015/07/S146.
Committee for Proprietary Medicinal Products (CPMP) Opinion Following an Article 10 Referral, CYKLO-f, Jul. 2000.
Consultation Document: Arm 30, Request to Reclassify a Product from Pom to P, Safeguarding public health, Medicines and Healthcare products Regulatory Agency, Feb. 7, 2007.
Consumer Medicine Information leaflet, "CYKLOKAPRON Tranexamic acid tablets and solution for injection", Pfizer Australia Pty Ltd 2010, 4 pgs.
Cooper, Jay, MD et al, "A randomized multicenter trial of safety and efficacy of the Nova Sure System in the treatment of Menorrhagia," *J. Am. Assoc. Gynecol. Laparosc.*, 2002; 9(4); 418-428.
Cooper, K. et al, "Five-year follow-up of women randomized to medical management or transcervical resection of the endometrium for heavy menstrual loss: clinical and quality of life outcomes," *Br. J. Obstet. Gynaecol.*, 2001; 108: 1222-1228.
Cooper, K., et al, "Comparison of microwave endometrial ablation and transcervical resection of the endometrium for treatment of heave menstrual loss; a randomized trial," *The Lancet*, 1999; 354.
Cooper, K.G. et al, "A randomized comparison of medical and hysteroscopic management in women consulting a gynecologist for treatment of heavy menstrual loss," *Brit. J. Obstet. Gynecol.*, 1997; 104:1360.
Cooper, Kevin G. et al, "Two-year follow up of women randomized to medical management or transcervical resection of the endometrium for heavy menstrual loss; clinical and quality of life outcomes," *Brit. J. Obstet. Gynecol.*, Mar. 1999; 106: 258-265.
Cote I., et al., "Work Loss Associated With Increased Menstrual Loss in the United States", *Obstet. Gynecol.*, 2002; 100; 683-7.
Coulter A., et al. "Quality of Life and Patent Satisfaction Following Treatment for Menorrhagia" Family Practice, 1994:11(4); 394-401.
Coulter, Angela et al, "Sharing decisions with patients: Is the information good enough?" *Brit. Med. J.*, 1999; 318: 318-322.
CPMP Opinion, *The European Agency for the Evaluation of Medical Products Evaluation of Medicines for Human Use*, Jul. 27, 2000—CPMP/902/00.
Crosignani, Pier Giorgio, MD et al, "Endometrial resection versus vaginal hysterectomy for menorrhagia: Long-term clinical and quality-of-life Outcomes," *Obstet. Gynecol.*, 1997, 177:95-101.
Crosignani, Pier Giorgio, MD et al, "Levonorgestrel-Releasing Intrauterine Device versus Hysteroscopic Endometrial Resection in the Treatment of Dysfunctional Uterine Bleeding," *Obstet. Gynecol.*, 1997, 90: No. 2.
Crotts, G et al., Development of an enteric coating formulation and process for tablets primarily composed of a highly water soluble organic acid: *Eur. J. Pharmaceut. Biopharmaceut*.51, (2001), 71-76.
Cyklokapron Tablets—Summary of product Characteristics (SPC), http://emc.medicines.org.uk/medicine/16512/SPC/Cycklokapron+Tablets/ downloaded on Aug. 26, 2009.
Cyklokapron, Tranexamic acid tablets and injection, Pharmacia, 2001.
Cyklokapron, Tranexamic acid Tablets and Tranexamic acid Injection, Antifibrinolytic agent, Pharmacia & Upjohn, p. 1-6 (2005).
Cyklokapron, Tranexamic acid Tablets and Tranexamic acid Injection, Product Description, p. 1-6 (2005).
Cyklokapron, Tranexamic acid tablets BP and Tranexamic acid injection BP, Product Monograph, Pfizer Canada Inc. Sep. 10, 2003.
Cyklokapron, Tranexamic Acid Tablets, Consumer Medicine Information. 3 pgs. (2001).
Cyklokapron, Tranexamic Acid, Data Sheet, http:/www.medsafe.govt.nz/Profs/datasheet/c/Cyckloprontabinj.htm downloaded Aug. 26, 2009, 7 pgs.
Cyklokapron® Package Insert, Pharmacia Canada, Inc., Mississauga, Ontario, (Nov. 2002).
De Souza, S.S., et al., "Hemoglobin levels predict quality of life in women with heavy menstrual bleeding", Arch. Gynecol. Obstet., Aug. 20, 2009.

Decision by USPTO dated Mar. 31, 2010 for Petition to Make Special, U.S. Appl. No. 12/714,181, 4 pgs.
Demers et al., "Gynaecological and Obstetric Management of Women with Inherited Bleeding Disorders," *J. Obstet. Gynecol. Can.*, No. 163, Jul. 2005, pp. 707-718.
Deyo, R.A., et al, "Reproducibility and Responsiveness of Health Status Measures; Statistics and Strategies for Evaluation", *Controlled Clinical Trials*: 1991, 12, 142S-158S.
Dockeray, C. et al, "The fibrinolytic enzyme system in normal menstruation and excessive uterine bleeding and the effect of Tranexamic Acid," *Eur. J. Obstet. Gynecol. Reprod. Biol.*, 24 (1987) 309-318.
Dollery et al., Therapeutic Drugs, Second Edition, pp. T150-T154 (1999), 8 pages.
Dow Chemical Co., Formulating for Controlled Release with METHOCEL Cellulose Ethers (35 pages) (1987).
Dow Chemical Co., METHOCEL as a Binding Agent for Tablet Production by Wet Granulation (14 pages) (1985).
Dowd N., et al, Pharmacokinetics of Tranexamic Acid during Cardiopulmonary Bypass, *Anesthesiology*, 2002; 97: 390-99.
Draft Guidance: Patient-reported Outcome Measures: Use in Medical Product Development to Support Labeling Claims, Feb. 2006.
Dubber, AHC., et al, "Amino Methyl Cyclohexane Carboxylic Acid (AMCHA), A New Synthetic Fibrinolytic Inhibitor," *Brit. J. Haematol.*, 1965; 11:237.
Dubber, AHC., et al, "Some Properties of the antifibrinolytic active isomer of Amino-Methylcyclohexane Carboxylic Acid," *The Lancet*, 1964; 2:1317-9.
Dueck, A., et al, "Meeting on the FDA Draft Guidance on Patient—Reported Outcomes," *Value in Health*, 2007: 10:suppl. 2, S64-S65.
Dunn, C.J., et al., "Tranexamic Acid; A Review of its Use in Surgery and Other Indications", *Drugs*, Jun. 1999 57 (6); 1005-1032.
Edlund, M., et al, "Reduction of menstrual blood loss in women suffering from idiopathic menorrhagia with a novel antifibrinolytic drug (Kabi2161)," *Brit. J. Obstet. Gynecol.*, 1995; 102; 913-917.
EMEA, "Committee for Proprietary Medicinal products Opinion Following an Article 10 Referral CYKLO-1 (Tranexamic acid)", EMEA Jul. 27, 2000, pp. 1-8.
Eriksson O., et al, "Pharmacokinetics of Tranexamic Acid after Intravenous Administration to Normal Volunteers," *Eur. J. Clin. Pharmacol.* 7, 375-380 (1974).
EuroQol Group, "Euro-Qol-a new facility for the measurement of health-related quality of life", *Health Policy*, 16 (1990) 199-208.
FDA Guidance for Industry: Patient-Reported Outcome Measures: Use in Medical Product Development to Support Labelling Claims; Dec. 2009.
FDA Guidance for Industry: Patient-Reported Outcome Measures: Use in Medical Product Development to Support Labelling Claims; Feb. 2006.
Ferguson, R.J., et al, "Use of the Reliable Change Index to evaluate Clinical significance in SF-36 Outcomes", *Qual. Life Res.*, 11:509-6, 2002.
Ferring B.V. v. Watson Labs., Inc. Order by Robert C. Jones, U.S. District Judge, District of Nevada, dated Feb. 6, 2013, 19 pgs.
Final Rejection dated Oct. 12, 2010 for Japanese Appl. No. 2006-521917 (with English translation), 6 pgs.
Flood, E.M., et al., "Psychometric evaluation of the Osteoporosis Patient Treatment Satisfaction Questionnaire (OPSAT-Q), a novel measure to assess satisfaction with bisphosphonate treatment in postmenopausal women" *Health and Quality of Life Outcomes* 2006, 4: 42.
Florence et al, "Novel Oral Drug Formulation, Their Potential in Modulating Adverse Effects" *Drug Safety*, 10(3) p. 233-266, 1994.
Fraser, I. S., "Estimating Menstrual Blood Loss in women with Normal and Excessive Menstrual Fluid Volume," *Obstet. Gynecol.*, 2001; 98: 806-14.
Friberg et al., "Bleeding disorders amount young women: A population-based prevalence study," *Acta Obstet. Gynecol. Scand.*, 2006, 85:200-206.
Frost, M., et al, "What is Sufficient Evidence for the Reliability and Validity of Patient-Reported Outcome Measures?" *Value in Health*, 2007; 10:suppl 2, S94-S105.

(56) References Cited

OTHER PUBLICATIONS

Garratt, A.M. et al, "SF 36 health survey questionnaire: II: Responsiveness to changes in health status in four common clinical conditions," *Quality in Health Care*, 1994; 3: 186-192.
Garratt, A.M. et al, "The SF 36 health survey questionnaire: an outcome measure suitable for routine use within the NHS?" *Brit. Med. J.*, 1993; 306.
Gath, D., et al, "Psychiatric disorder and gynaecological symptoms in middle aged women; a community survey," *Brit. Med. J.*, 1987; 294: 213.
Giangrande, P.L.F., "Tranexamic Acid", http://www.Medicine ox.ac.uk/ohc/tranexam.htm, p. 1 downloaded Nov. 4, 2004.
Gleeson, N. C. et al, The effect of tranexamic acid on measured menstrual loss and endometrial fibrinolytic enzymes in dysfunctional uterine bleeding, *Acta Obstet. Gynecol. Scand.* 1994; 73: 274-277.
Gorgen, H., et al., "Use of the Levonorgestrel-IUS in the treatment of menorrhagia: assessment of quality of life in Turkish users", *Arch. Gynecol. Obstet.*, pub. Online Nov. 19, 2008.
Greenberg Quinlan Rosner Research Inc., "Survey of Women Who Experience Heavy Menstrual Bleeding" for Nation Women's Health Resource Center, Nov. 15, 2005.
Gumpel, J.M. et al., "Self-administered Clinical Questionnaire for outpatients", *Brit. Med. J.*, 174, 209-212. (1974).
Guyatt, G.H., MD et al, "Interpreting treatment effects in randomized trials," *Brit. Med. J.*, 1998; 316.
Guyatt, G.H., MD et al, "Postscript," *Controlled Clinical Trials*, 1991; 12; 266S-269S.
Guyatt, G.H., MD et al, Measuring disease-specific quality of life in clinical trials, *Can. Med. Assoc. J.*, 1986; 134: 889.
Hallberg, Leif et al, "Menstrual Blood Loss-A Population Study," *Goran, Acta Obstet. Gynecol. Scand.*, 1966; 45:320.
Hays, J. et al, "Effects of Estrogen plus Progestin on health Related Quality of Life" *N. Engl. J. Med.*, 2003, 348;1839-54.
Hays, R. D. et al, "The Rand 36-Item Health Survey 1.0," *Health Economics*, 1993; 2: 217-227.
Heavy Menstrual Bleeding, Clinical Guideline, Jan. 2007.
Higham, J.M. et al, "Risk-Benefit Assessment of Drugs Used for the Treatment of Menstrual Disorders," *Drug Safety*, 1991; 6(3): 183-191.
Hoylaerts, M., et al, "Studies on the Mechanism of the Antifibrinolytic Action of Tranexamic Acid," *Biochim. Biophys. Acta*, 673 (1981) 75-85.
Hurskainen, R., et al, "Combined Laboratory and diary method for objective Assessment of menstrual Blood loss"; *Acta. Obstet. Gynecol. Scand.* 1998, 77; 201-204.
Hurskainen, R., et al, "Quality of life and cost-effectiveness of levonorgestrel-releasing intrauterine system versus hysterectomy for treatment of menorrhagia: a randomized trial," *The Lancet*, 2001, 357.
Hypromellose, Wikipedia definition, p. 1-3 http://en. Wikipedia.org/wiki/Hypromellose, downloaded on Jan. 16, 2009.
Information Sheet A.D.A.M., Inc. 1997-2007 (Internet)"Tranexamic acid", submitted to the USPTO on May 6, 2010, 6 pgs.
Information Sheet: Transamin Capsules, with Product Information: Transamin Tablets 500 mg dated Feb. 1998.
Information Sheet: Transamin Otlo Pharmaceuticals, cap, tbs, injection, submitted to the USPTO on May 6, 2010.
International Search Report from PCT/US2004/023528 dated Jan. 7, 2005.
International Search Report from PCT/US2005/20558 dated Nov. 8, 2005.
International Search Report from PCT/US2005/20563 dated Nov. 10, 2005.
Interview Summary issued by dated Apr. 19, 2011 for U.S. Appl. No. 11/346,710, 3 pgs.
Investigative report dated Apr. 7, 2010 and prepared by Chief Investigator D.C. Sharma of ClueWise Services, Pvt. LTD. (India) concerning information sought on Mefro Pharmaceuticals and Terrance Pharma (both of India), specifically in relation to a Trexamic Rx product (tranexamic acid) 3 pgs.

Jaeschke, R., et al, "Ascertaining the Minimal Clinically Important Difference," *Controlled Clinical Trials*, 1989; 10:407-415.
Jaeschke, R., et al, "Interpreting Changes in Quality-of-Life Score in N of 1 Randomized Trials," *Controlled Clinical Trials*, 1991; 12:226S-233S.
Janet Vaughn, Director, Regulatory Affairs, Watson Laboratories Florida, Notification of Certification of Invalidity and/or Noninfringement for U.S. Patent No. 8,022,106 Pursuant to Section 505(j)(2)(B)(iv) of the Federal Food, Drug and Cosmetic Act, dated Oct. 12, 2011 (15 pages).
Janet Vaughn, Director, Regulatory Affairs, Watson Laboratories Florida, Notification of Certification of Invalidity and/or Noninfringement of U.S. Patent No. 7947739 Pursuant to Section 505(j)(2)(B)(iv) of the Federal Food, Drug, and Cosmetic Act, dated May 24, 2011 (16 pages).
Janet Vaughn, Director, Regulatory Affairs, Watson Laboratories Florida, Notification of Invalidity and/or Noninfringement for U.S. Patent No. 8,273,795 Pursuant to §505(j)(2)(B)(iv) of the Federal Food, Drug, and Cosmetic Act, dated Nov. 5, 2012, 11 pgs.
Jenkinson, C. et al, "Measuring change over time: a comparison of results from a global single item of health status and the multi-dimensional SF-36 health status survey questionnaire in patients presenting with menorrhagia," *Quality of Life Survey*, 1994; 3:317-321.
Jenkinson, C., et al "Making sense of ambiguity: evaluation of internal reliability and face validity of the SF 36 questionnaire in women presenting with menorrhagia," *Quality in Healthcare*, 1996; 5: 9-12.
Jones, G.,' et al, "Health-related quality of life measurement in women with common benign gynecologic conditions: A systematic review," *A. J. Obstet. Gynecol. Rev.*, 2002; 187; 501-11.
Juniper, E., et al, "Determining a Minimal Important Change in a Disease-Specific Quality of Life Questionaire", *J. Clin. Epidemiol.* vol. 47, No. 1, 81-87, 1994.
Kadir, R.A. et al, "Quality of life during menstruation in patients with inherited bleeding disorders," *Hemophilia*, 1998; 4: 836-841.
Kadir, R.A., et al, "Management of excessive menstrual bleeding in women with hemostatic disorders," *Fertility and Sterility*, 2005; 865(5), 1352-1359.
Kaller H., Enterale Resorption, Verteilung und Elimination von 4-Ainomethylcyclohexancarbonsaure (AMCHA) und a-Aminocapronsure (ACS) beim Menschen, *Naunyn-Schmiedeberts Arch. Pharmak. U. Exp. Path.* 256, 160-168 (1967).
Kennedy, A., et al, "Effects of Decision Aids for Menorrhagia on Treatment Choices, Health Outcomes and Costs," *J. Am. Med. Assoc.*, 2002; 288: 2701-2708.
Kirshner, B., et al, "A Methodological Framework for Assessing Health Indices," *J. Chron. Dis.*, 1985; 38: No. 1, 27-36.
Kjerulff, K.H., et al. "Patient satisfaction with results of hysterectomy", *Am. J. Obstet. Gynecol.*, 2000; 183: 1440-7.
Kouides, PA et al, "Multisite management study of menorrhagia with abnormal laboratory haemostasis: a prospective crossover study of intranasal desmopressin and oral tranexamic acid," *Brit. J. Haemotol.*, 2009; 145(2): 212-220.
Kouides and Kadir, "Menorrhagia associated with laboratory abnormalities of hemostasis: epidemiological, diagnostic and therapeutic aspects," *J. Thromb. Haemost.*, 2007, 5 (Supple. 1): 174-182.
Kriplani et al, "Role of tranexamic acid in management of dysfunctional uterine bleeding in comparison with medroxyprogesterone acetate," *J. Obstet. Gynecol.*, vol. 26, No. 7 (2006), pp. 673-678.
Kuppermann, M., et al, "Effect of Hysterectomy vs. Medical Treatment on Health-Related Quality of Life and Sexual Functioning," *J. Am. Med. Assoc.* 2004; Mar. 2004; 291: No. 12.
Lakhani, K. P. et al, "Uterine artery blood flow parameters in women with dysfunctional uterine bleeding and uterine fibroids: the effects of tranexamic acid," *Ultrasound Obstet. Gynecol.* (1998); 11: 283-285.
Lamping D.L., et al., "Development and Validation of an Audit Instrument: the Prostate Outcomes Questionnaire", *Brit. J. Urol.*, 1998, 82, 49-62.
Lamping, D.L. et al, "Development and validation of the menorrhagia outcomes questionnaires," *Brit. J. Obstet. Gynecol.*, 1998; 105: 766-779.

(56) References Cited

OTHER PUBLICATIONS

Lee et al., Controlled-Release Drug-Delivery Systems, Chapter 47 in Gennaro et al., Remington: The Science and Practice of Pharmacy, 20th Edition, Lippincott, Williams and Wilkins, pp. 903-929 (2000).
Lee et al., "Treatment of Menorrhagia with Tranexamic Acid," *Fertility and Sterility*, Oct. 18, 1997, suppl. 1, pg. 96.
Lee, J. et al, "Treatment of Menorrhagia with Tranexamic Acid," *J. Soc. Obstet. Gynaecol. Can.*, 2000:22(109):794-8.
Leidy, N. K. et al., "Recommendations for Evaluation the Validity of Quality of Life Claims for Labeling and Promotion", ISPOR, *Value in Health*, 1999; 2(2), 113-127.
Lethaby A, Farquhar C, Cooke I. Antifibrinolytics for heavy menstrual bleeding. *Cochrane Database of Systematic Reviews* 2000, Issue 4. The Cochrane Library, 2008 Issue 2.
Lethaby et al., Antifibrinolytics for Heavy Menstrual Bleeding, Cochrane Database of Systematic Reviews, Issue 4, 2002, (61 pp).
Lethaby, A. et al, "Antifibrinolytics for heavy menstrual bleeding (Review)," *The Cochrane Collaboration*, 2008; issue 24.
Lethaby, A., et al, "Antifibrinolytics for heavy menstrual bleeding, (Review)" *The Cochrane Collaboration*, 2002; Issue 4.
Levy et al., "Consider this option for heavy menstrual bleeding," *J. Fam. Pract.*, 2011, 60(7):410-412.
Liu, Z., et al., "A Systematic Review Evaluation health-Related Quality of Life, Work Impairment, and Health-Care Costs and Utilization in Abnormal Uterine Bleeding" ISPOR, *Value in Health*, 2007; 10(3), 183-194.
Lockhart, I., Comments on MHRA Consultation Arm 39; Request to Reclassify Cyklo-F 500 Mg. Tablets (Tranexamic Acid) from Prescription only Medicine (POM) to Pharmacy available (P); Royal College of Physicians of Edinburgh, Feb. 27, 2007.
Lohr, K., et al., Evaluating Quality of Life and Health Status Instruments: Development of Scientific Review Criteria, *Clin. Therapeutics*, vol. 18, No. 5, 1996, 979.
Longstaff, C., "Studies on the mechanisms of action of aprotinin and tranexamic acid as plasmin inhibitors and antifibrinolytic agents," *Blood Coagulation and Fibrinolysis*, vol. 5, 1994, pp. 537-542.
Lydick E., et al., "Interpretation of quality of life changes", *Quality of Life Research*, 1993; 2, 221-226.
Mannucci, P.M., "Hemostatic Drugs", *New England J. Medicine*, vol. 339(4); 245-253. (1998).
Marjoribanks, J. et al, "Surgery versus medical therapy for heavy menstrual bleeding (Review)", The Cochrane Library, 2009, Issue 2.
Martindale—revision Nov. 28, 2001, Monograph, tranexamic acid (1726j).
McHorney, C.A. et al, "The MOS 36-Item Short-Form Health Survey (SF36) II, Psychometric and Clinical Test of Validity in Measuring Physical and Mental Health Constructs", *Med. Care*, 1993; 31(3): 247-263.
McHorney, C.A. et al, "The MOS 36-Item Short-Form Health Survey (SF36) III. Psychometric and Clinical Test of Data Quality, Scaling Assumptions, and Reliability Across Diverse Patent Groups", *Med. Care*, 1994; 32(1): 40-66.
Mehta, B.C. et al, "Epsilon-Amino-Caproic Acid in the Treatment of Menorrhagia," *J. Postgrad. Med.*, 1977; 23(3): 121-123.
Melander, B., et al, "Biochemistry and Toxicology of Amikapron®; The Antifibrinolytically Active Isomer of (AMCHA.) (A Comparative Study with Aminocaproic Acid)," *Acta Pharmacol. Toxicol.* 1965, 22, 340-352.
Milsom, I. et al. "A comparison of flurbiprofen, tranexamic acid, and a levonorgestrel-releasing intrauterine contraceptive device in the treatment of idiopathic menorrhagia," *Am. J. Obstet. Gynecol.*, 1991; 194: 879-883.
Mohri, H., "High Dose of Tranexamic Acid for Treatment of Severe Menorrhagia in patients with von Willebrand Disease," *J. Thromb. Thrombolysis*, 14(3), 255-257, 2002.
Monograph Health Canada; Cyklokapron; solution: for IV Use, date May 2005.
Monograph: British Nat. Formulary No. 43, 2002 sec. 2. 11 Antifibrolytic drugs and haemostatics; Tranexamic acid No. 123.
Moos, K., MDQ Form C, published by Western Psychological Services, 1989.
National Center for Women's and Children's Health: Heavy Menstrual Bleeding Full Guideline Draft, (Jul. 2006).
New Zealand Working Party Guidelines, "An evidence-based guideline for the management of heavy menstrual bleeding", N Z Medical Journal, 1999, 112; 174-7.
Nice Clinical Guideline 44, "Heavy Menstrual bleeding", Jan. 2007.
Nilsson, I., "Clinical pharmacology of aminocaproic and tranexamic acids," *J. Clin. Pathol.*, 33, Suppl. (Roy Coll Path), 14, 41-47. (1980).
Nilsson, L and Rybo, G, "Treatment of Menorrhagia with an Antifibrinolytic Agent, Tranexamic Acid (AMCA)," *Acta Obst. Gynecol. Scand.*, 46, 572, 1967.
Notice of Allowance dated Apr. 8, 2011, U.S. Appl. No. 12/714,181, 9 pgs.
Notice of Allowance dated Aug. 5, 2011 for U.S. Appl. No. 12/433,510, 7 pgs.
Notice of Panel Decision from Pre-Appeal Brief Review dated Feb. 7, 2013 for U.S. Appl. No. 12/433,247, 2 pgs.
Notice of Rejection dated Aug. 17, 2010 for Japanese Appl. No. 2007-523556 (with English translation), 11 pgs.
Notice of Rejection dated Aug. 2, 2011, Japanese Appl. No. 2006-521917, 3 pgs.
Notice of Rejection dated Aug. 2, 2011, Japanese Appl. No. 2011-028472, 7 pgs.
Notice of Rejection dated Dec. 20, 2011, Japanese Appl. No. 2007-523555, 3 pgs.
Notice of Rejection dated Jan. 29, 2013 for Japanese Appl. No. 2011-062281, 5 pgs.
Notice of Rejection dated Oct. 25, 2011, Japanese Appl. No. 2007-523556, 2 pgs.
Notice of Rejection dated Sep. 29, 2009 for Japanese Appl. No. 2006-521917 (with English translation), 25 pgs.
Notice of Rejection dated Sep. 3, 2010 for Japanese Appl. No. 2007-523555 (with English translation), 11 pgs.
Office Action (Examiner Interview Summary Record) issued by dated Oct. 28, 2008 for U.S. Appl. No. 10/631,371, 2 pgs.
Office Action (Final Rejection) issued by dated Dec. 6, 2010 for U.S. Appl. No. 11/346,710, 12 pgs.
Office Action (Final Rejection) issued by dated Jun. 14, 2007 for U.S. Appl. No. 10/631,371, 9 pgs.
Office Action (Final Rejection) issued by dated Sep. 9, 2010 for U.S. Appl. No. 12/220,241, 8 pgs.
Office Action (final) issued by dated Jun. 28, 2012 for U.S. Appl. No. 12/433,247, 21 pgs.
Office Action (final) issued by dated Aug. 25, 2010, U.S. Appl. No. 12/714,181, 11 pgs.
Office Action (Final) dated Aug. 9, 2011 for U.S. Appl. No. 12/228,489, 38 pgs.
Office Action (Final) dated May 11, 2011 for U.S. Appl. No. 12/433,510, 4 pgs.
Office Action (Non-final) dated Oct. 25, 2011 for U.S. Appl. No. 12/433,247, 18 pgs.
Office Action (Non-Final) dated Dec. 15, 2006 for U.S. Appl. No. 10/631,371, 6 pgs.
Office Action (Non-Final) dated Mar. 13, 2008 for U.S. Appl. No. 10/631,371, 7 pgs.
Office Action (Non-Final) dated Mar. 18, 2010 for U.S. Appl. No. 11/346,710, 9 pgs.
Office Action (Non-Final) dated Feb. 5, 2010 for U.S. Appl. No. 12/220,241, 7 pgs.
Office Action (Non-Final) dated Jan. 23, 2008 for U.S. Appl. No. 11/072,162, 6 pgs.
Office Action (Non-Final) dated Jul. 30, 2010 for U.S. Appl. No. 12/433,408, 7 pgs.
Office Action (Non-Final) dated May 10, 2010 for U.S. Appl. No. 12/433,510, 9 pgs.
Office Action (Non-Final) dated Oct. 28, 2010 for U.S. Appl. No. 12/433,510, 11pgs.
Office Action (non-final) idated Apr. 27, 2010, U.S. Appl. No. 12/714,181, 8 pgs.
Office Action (non-final) dated Jul. 1, 2010, U.S. Appl. No. 12/714,181, 11 pgs.

(56) References Cited

OTHER PUBLICATIONS

Office Action (Non-Final) dated Nov. 8, 2010 for U.S. Appl. No. 12/228,489, 16 pgs.
Office Action (non-final) dated Dec. 3, 2010, U.S. Appl. No. 12/714,181, 17 pgs.
Office Action (Non-Final) dated Oct. 25, 2011 for U.S. Appl. No. 12/433,247, 33 pgs.
Office Action (Restriction Requirement) dated May 17, 2011 for U.S. Appl. No. 12/433,247, 9 pgs.
Office Action (Restriction Requirement) dated Aug. 17, 2009 for U.S. Appl. No. 11/346,710, 7 pgs.
Office Action (Restriction Requirement) dated Aug. 25, 2006 for U.S. Appl. No. 10/631,371, 6 pgs.
Office Action (Restriction Requirement) dated Jul. 20, 2010 for U.S. Appl. No. 12/228,489, 5 pgs.
Office Action (Restriction Requirement) dated Sep. 5, 2012, U.S. Appl. No. 12/770,185, 5 pages.
Office Action (Non-final) dated Feb. 28, 2013, U.S. Appl. No. 12/770,185, 5 pages.
Office Action (Restriction Requirement) dated Feb. 17, 2010 for U.S. Appl. No. 12/433,408, 8 pgs.
Office Action (Restriction Requirement) dated Nov. 27, 2007 for U.S. Appl. No. 11/072,162, 9 pgs.
Office Action (Restriction Requirement) dated Oct. 20, 2009 for U.S. Appl. No. 12/220,241, 9 pgs.
Office Action (Restriction Requirement) dated Feb. 14, 2008 for U.S. Appl. No. 11/072,194, 7 pgs.
Office Action (Restriction Requirement) dated Sep. 12, 2012 for U.S. Appl. No. 13/230,902, 6 pgs.
Office Action (Restriction Requirement) dated Feb. 11, 2013 for U.S. Appl. No. 13/620,148, 7 pgs.
Office Action dated Jun. 29, 2011 for U.S. Appl. No. 12/283,694, 27 pgs.
Office Action dated Mar. 1, 2012 for U.S. Appl. No. 12/283,694, 18 pgs.
Ogston. D, "Current Status of Antifibrinolytic Drugs," *Blood Reviews*, 1989; (3): 1-4.
Ong Y.L. et al, "Menorrhagia in von Willebrand disease successfully treated with single daily dose tranexamic acid," *Haemophilla*, 1998,4: 63-65.
Osoba, D., et al, "Evaluating Health-Related Quality of Life in Cancer Clinical Trials: The National Cancer Institute of Canada Clinical Trials Group Experience," *Value in Health*, 2007; 10: suppl 2, 1098-3015/07/S138.
Package Leaflet: Information for the User, Cycklo-f-500 mg film-coated tablet, Tranexamic acid (Mar. 2, 2007), 3 pgs.
Package Leaflet: Information for the user, Cyklonova 500 mg film-coated tablet. Leaflet approved Dec. 12, 2005. p. 1-3.
Park, Serena and Farquhar, CM, "A survey of practice preferences and attitudes of the New Zealand Guidelines for the management of heavy menstrual bleeding", Aust NZ J Obstet. Gynaecol 2002; 42, 4:376, p. 377-80.
Patent Abstracts of Japan Publication No. JP 07206660, *External Preparation for Skin*, Published Aug. 8, 1995.
Patent Abstracts of Japan Publication No. JP 09124878, *Gel Composition*, Published May 13, 1997.
Patent Abstracts of Japan Publication No. JP 06219942, *Gelatin Capsule Preparation Mixed With Tranexamic Acid*, Published Aug. 9, 1994.
Patent Abstracts of Japan Publication No. JP 0925542, *Composition for Oral Cavity Application*, Published Sep. 30, 1997.
Patent Abstracts of Japan Publication No. JP 57059847, *4-Aminomethylcyclohexanecarboxylic Acid Derivative*, published Apr. 10, 1982.
Patrick, D.L. et al, "Quality of Life of Women with Urinary Incontinence, Further development of the incontinence quality of Life Instrument (1-QOL)", Urology, 53: 71-76, 1999.
Patrick, D.L., et al, "Assessing the Clinical Significance of health related quality of life (HrQOL) improvements in anaemic cancer patients receiving epotin-alfa", *Eur. J. Cancer*, 39 (2003) 335-345.
Patrick, D.L., et al, "Patient-Reported Outcomes to Support Medical Product Labeling Claims: FDA Perspective," Patrick, D.L., et al, "Patient-Reported Outcomes to Support Medical Product Labeling Claims: FDA Perspective," *Value in Health*, 2007; 10: suppl 2, 1098-3015/07/S 125.
Pawar, A. et al., "Perceptions about quality of life in a school-based population of adolescents with menorrhagia: implications for adolescents with bleeding disorders", *Haemophilia*, 2008, 14, 579-583.
Peterson et al., Treatment of Menorrhagia with Tranexamic Acid, *Acta Obstet. Gynecol. Scand.*, 1983, Supp. 116, p. 70, 115.
Philipp, C.S., et al, "Development of a screening tool for identifying women with menorrhagia for haemostatic evaluation," *Am. J. Obstet. Gynecol.*, 2008; 1998: Issue 2, 163.
Philipp, C. S. et al., "Age and the Prevalence of Bleeding Disorders in women with Menorrhagia", Obstet. Gynecol. 2005; 105: 61-6.
Pilbrant, A., et al, "Pharmacokinetics and Bioavailability of Tranexamic Acid," *Eur. J. Clin. Pharmacol.*, (1981) 20: 65-72.
Popo, V., MHRA, Consultant Doc.: ARM 39, Request to Reclassify a product from POM to P; Cyklo-F, Feb. 7, 2007.
Prentice, C.R.M., "Indications for Antifibrinolytic Therapy," *Thrombos. Diathes. Haemorrh. (Stuttg.)*, 1975; 34: 634.
Preston J. T., et al, "Comparative study of tranexamic acid and norethisterone in the treatment of ovulatory menorrhagia," *Brit. J. Obstet. Gynecol.*, May 1995, vol. 102, pp. 401-406.
Price list detailing the prices of numerous Mefro Pharmaceutical (P) LTD Products, including Tab, Trexamic and Tab trexamic-M (Reference A13), submitted to USPTO on Jul. 6, 2010, 8 pgs.
Product catalog of Mefro Pharmaceuticals (P) LTD. that lists Tab Trexamic and Tab Trexamic-M as available products (Reference A12), submitted to USPTO on Jul. 6, 2010, 8 pgs.
Product Information Cyklokapron Pharmacia; South Africa; 500 mg tablets, 500 mg IV, 1g effervescent tablets; package insert dated Dec. 1999.
Product Information Cyklokapron® Pfizer Australia, most recent Amendment Mar. 11, 2008, pp. 1-8.
Product Information Kalnex Capsules (250mg), tablets (500 mg,) Injection, 1991.
Product Information, Cycklokapron, Tranexamic acid (CAS 1197-18-8), 26 pgs., (Mar. 11, 2008).
Product Information, Tranexamic Acid, downloaded from http://csi.micromedex.com/DKS/DATA/MT/MTMI/1726-j.HTM?Top=Yes (1 of 9) Nov. 4, 2003 10:05:51 AM.
Product Information: Amchafibrin, 500 mg, submitted to USPTO on May 6, 2010.
Product Information: Cyklokapron "Media, Pfizer," Injection, 500 mg tablets, dated Oct. 24, 2006.
Product Information: Cyklokapron Injection, Ampoules 500 mg per 5ml, Pharmacia Limited UK, authorization date Feb. 9, 1987.
Product Information: Cyklokapron Pharmacia; US, 500 mg tablets and injection; package insert dated Oct. 2000.
Product Information: Cyklokapron tablets and injection; 100 mg/1ml water, Pharmacia & Upjohn revision Jun. 2008.
Product Information: Cyklonova 500 mg film coated tablets; product information date Oct. 5, 2007.
Product Information: Daiichi Pharmaceutical Co. Ltd., Transamin Injection and Transamin S injection; 250 mg/5 ml, 250 mg/2.5 ml and 1 g/10ml. 14 pgs. (1998).
Product Information: Dexa Medica, Traexid injection, 5% and injection 10% 9 p. (2008).
Product Information: Proklot film coated tablet, 500 mg, submitted to USPTO on May 6, 2010.
Product Information: Teva Pharmaceutial Industries Ltd., HEXAPRON; 500 mg/5ml, 3 p. (2003).
Product Information: Tranexid, 250 mg capsules, 500 mg membrane coated tablets http://www.dexamedica, com/printview.php?cid+3& id=62, Sep. 11, 2008, 6 pgs.
Product Information: Tranfib, tablets and injection, submitted to USPTO on May 6, 2010.
Product Information: Transamin Capsules, 250 mg tablets, 500 mg tablets, 50% powder, product information revision Jun. 2005.
Product Information: Transamin Capsules dated Feb. 1998.

(56) References Cited

OTHER PUBLICATIONS

Product Information: Trexamic Rx (Tranexamic acid tablets BP 500 mg), marketed by Metfro Pharmaceuticals, Ltd, manufactured by Terrance Pharmaceuticals, Ltd., p. 1, (2001).

Product Information: Cyklokapron—tranexamic acid injection solution, 100 mg/1 ml. Pharmacia & Upjohn revision Jun. 2008.

Product Information: Cyklokapron KabiVitrumAB; US, 500 mg tablets and injection; package insert dated Jan. 1987.

Product Information: Cyklokapron tablets (Pfizer Au, approval 2001) with PI version pfpcykl10308; PI Medsafe data sheet New Zealand 2008 (film coated tablet); and Pfizer data sheet (Spanish).

Product Information: Hemostan 250, 500 mg capsules, injection, submitted to USPTO on May 6, 2010.

Product Information: Tranon 500 mg film coated tablet, product information approved Apr. 16, 2008.

Product Information Sheet Lexi-comp: Tranexamic Acid, Brand names, 5 pgs. (2008).

Product Monograph: Cyklokapron: Pfizer Canada Control No. 086534; Tranexamic acid tablets BP and Tranexamic acid injection BP date: Sep. 10, 2003, control No. 086534.

Production Information: Cyklo-f 500 mg film coated tablet, authorization Jan. 31, 1997.

Production Information: Cyklokapron—tranexamic acid injection solutions, 100 mg/1ml. Pharmacia & Upjohn revision Jul. 2005, product registration, Jul. 31, 1968 (Dutch Language).

Production Information: Cyklokapron Tablets 500 mg. product authorization Feb. 2005.

Production Information: Cyklokapron Tablets 500 mg. film coat, product Jul. 31, 1968 with product information: Cyklokapron 100 mg effervescent tablets, product authorization Dec. 7, 1995.

Protheroe, J., et al "The role of primary care in the diagnosis and management of menorrhagia: a qualitative study of women with menorrhagia," Primary Health Care Research and Development 2005: 6: 21-22.

Puigdellivol, E. et al, "Pharmacokinetics and absolute bioavailability of intramuscular tranexamic acid in man," International Journal of Clinical Pharmacology, Therapy and Toxicology, 1985; 23; No. 6, 298-301.

Quantification of Menstrual Blood Loss, Review, The Obstetrician & Gynecologist, 2004; 6: p. 88-92.

Quixil solutions for sealant, date of first authorization Sep. 1999.

Radloff, L.S., "The CES-D Scale: A Self-Reported Depression Scale for Research in the General Population", App. Psychological. Measurement, 1977; 1(3), 385-401.

Ragab, M.I. et al, The Use of Tranexamic Acid (AMCA) in IUDs as an Anti-bleeding agent, Int. J. Gynacol Obstet, 1976; 14:137-141.

Ranzcog, NHC Guidelines, Mar. 1999.

Reid, P.C., et al., "Assessment of Menstrual Blood Loss using a Pictorial Chart: a Validation Study" Brit. J. Obstet. Gynaecol., Mar. 2000, vol. 107, pp. 320-322.

Revicki, D.A., et al, "Interpreting and Reporting Results Based on Patient-Reported Outcomes," Value in Health 2007; 10: suppl. 2, 1098-3015/07/S138.

Richter, H.E., et al., "Medroxyprogesterone acetate treatment of abnormal uterine bleeding: Factors predicting satisfaction", Am. J. Obstet. Gynecol., Jul. 2003, pp. 37-42.

Ross Maclean, VP Global Regulatory Affairs, Letter from Apotex Inc. to Ferring B.V., dated Nov. 5, 2012, 10 pg.

Rothman, M.L. et al., "Patient Reported Outcomes: Conceptual Issues", Value in Health, vol. 10 Supp. 2, 2007, pp. S66-S75.

Rounds et al., Answer, Affirmative Defenses and Counter-Claims for Complaint for Patent Infringement, dated Feb. 28, 2013, 21 pp.

Ruta, D.A. et al, "Patient centered assessment of quality of life for patients with four common conditions," Quality in Health Care, 1999; 22-29.

Ruta, D.A. et al, Assessment of patients with Menorrhagia: how valid is a structured clinical history as a measure of health status, Quality of Life Research, 1995; 4: 33-40.

Ruta, D.A. et al, SF 36 health survey questionnaire: 1. Reliability in two patient based studies, Quality in Health Care, 1994; 3: 180-185.

Rybo G., "Plasminogen Activators n the Endometrium, I. Methodological Aspects," Acta Obstet. Gynecol. Scand. 45, 411, 1966.

Rybo, "Tranexamic acid therapy—effective treatment in heavy menstrual bleeding." Therapeutic Advances, 1991; issue 4.

Santer, M. et al., "What aspects of periods are most bothersome for women reporting heavy menstrual bleeding? Community survey and qualitative study", BMC Women 's Health 2007, 7:8.

Scientific Advisory Committee, "Assessing health status and quality of life instruments; Attributes and review criteria", Quality of Life Research 11: 193-205, 2002.

Scientific Conclusions and Grounds for Amendment of the Summary of Product Characteristics Presented by the EMEA, Annex 1, p. 1-15, submitted to USPTO on May 6, 2010.

Sculpher, M.J., et al., "Randomized trial comparing hysterectomy and transcervical endometrial resection: effect on health related quality of life and costs two years after surgery", Brit. J. Obstet. Gynaecol., 1996, 103,142-149.

Shankar, M. et al, "Review of quality of life: Menorrhagia in women with or without inherited bleeding disorder," Haemophilia, 2008; 14: 15-20.

Shapley, M., et al. "An epidemiological survey of symptoms of menstrual loss in the community", Brit. J. Gen. Pract., 2004, 54; 359-363.

Shapley, M., et al. "Why women consult with increased vaginal bleeding: a case-control study", Brit. J. Gen. Pract., 2002, 52, 108-113.

Shaw, R. W. et al, "Perceptions of women on the Impact of menorrhagia on their health using multi-attribute utility assessment," Brit. J. Obstet. Gynecol., Nov. 1998; 105: 1155-1159.

Shaw, R.W., "Assessment of medical treatments for Menorrhagia," Brit. J. Obstet. Gynecol. 1994; vol. 101, suppl. 11:15-18.

Shin-Yakuzaigaku Souron (New General Pharmaceutics), Nankodo, revised edition vol. 3, Apr. 10, 1987, pp. 287-291 (Note: An English translation of Table 10.2 is included), 6 pgs.

Siddiquil, Shahnaz Hasan, "Spectrum of Dysfunctional Uterine Bleeding and its Conservative Management", JCPSP 2003, vol. 13 (7):375-377.

Siegel, J.E. and Kouldes, P.A. "Menorrhagia from a hematologist's point of view. Part II: Management" Hemophilia (2002), 8, p. 339-347.

Silverman, E., "Your Drug Target Audience", The Scientist, Oct. 2007; 65-70.

Sindet-Pedersen, "Distribution of tranexamic acid to plasma and saliva after oral administration and mouth rinsing: a pharmacokinetic study," J. Clin. Pharmacol. 1987; 27; 1005.

Sloan, J.A., et al, "The Mayo Clinic manuscript Series Relative to the Discussion Dissemination, and Operationalization of the Food and Drug Administration Guidance on Patient Reported Outcomes", ISPOR, Values in Health, 2007, 10 Supp2., S69-S63.

Sloan, J.A., et al. "Analysis and Interpretation of Results Based on Patient Reported Outcomes", ISPOR, Values in Health, 2007, 10, Supp2., S106-S115.

Smith, N.D., "Quality of Life Studies From the Perspective of an FDA Reviewing Statistician", Drug Inf. J. 1993, 27,617-623.

Snyder, C.F., et al., "Patient Reported Outcome Instrument Selection: Designing a Measuring Strategy" ISPOR, Values In Health, 2007, 10 Supp2., S76-S85.

Spies, J.B., et al., "The Fibroid Registry; Symptom and Quality of Life Status 1 year After Therapy", Obstet. Gynecol. 2005, 106; 1309-18.

Spies, J.B., et al., "The UFS-QOL, a New Disease-Specific Symptom and Health-Related Quality of Life Questionnaire for Leiomyomata", Obstet. Gynecol. 2002, 99; 290-300.

Srinil, S., et al., "Treatment of Idiopathic Menorrhagia with Tranexamic Acid", J Med Assoc. Thai 2005; 88(Supp1.2); S1-6.

Stanford School of Medicine, Div. Imm. & Rheu., "The Health Assessment Questionnaire", Jan. 19, 2001.

(56) References Cited

OTHER PUBLICATIONS

Stavchansky and McGinity, "Bioavailability in Tablet Technology", Ch. 6, in Lieberman et al., Pharmaceutical Dosage Form, 2$^{nd}$ Ed., vol. 2, Marcel Dekker, pp. 349-569 (1990).
Stirk, J., et al., "Sensitivity and Specificity of Observer and Self-Report Questionnaires in major and minor Depression Following Myocardial Infarction" *Psychosomatics*, 2001: 42: 423-428.
Stirrat, Gordon M., "Choice of treatment for menorrhagia," *The Lancet*, Jun. 26, 1999, vol. 353, pp. 2175-2176.
Svahn C M, et al, "Absorption of Tranexamic Acid as a Prodrug in Healthy Volunteers," *Arzneim. Forsch. Drug* 38(1), Nr. 5 (1988).
Svahn, C. M. et al, "Tranexamic Acid Derivatives with Enhanced Absorption", *J. Med. Chem.*, 1986, vol. 29, No. 4. p. 448-453.
Tapanainen, Juha S., "Medical Management of Menstrual Disorders", J.S. Tapanainen/International Congress Series 1266 (2004) 63-68.
Testa, M.A., et al., "Methods for Quality of Life Studies", *Ann. Rev. Public Health*, 1994, 15:535-59.
Thorsen S., "Differences in the Binding to Fibrin of Native Plasminogen and Plasminogen Modified by Proteolytic Degradation Influence of ω-Aminocarboxylic Acids," *Biochim. Biophys. Acta*, 393 (1975) 55-65—Elsevier Scientific Publishing Company, Amersterdam.
Tranexamic acid Product Description, p. T151-154 (1985).
Transamin Capsules (250mg), Tranexamic Acid Preparation, Product Description 2 pgs. (Aug. 1995).
Transamin, Transamin cap approved prescribing info, MIMS Malaysia, downloaded Mar. 8, 2010 http://www.mims.com/Page.aspx?menuid=Transamin+cap&CTRY=MY&brief., pg. 1-6.
Transmin Tablets 500 mg, Tranexamic Acid Preparation, Product Description, 1 pg. (1998).
Treatment and Management of Women with Bleeding Disorders, clinical trials.gov (2005), downloaded from http://clinicaltrials.gov/?ct2/show/NCT00111215?cond=%22von+Willebrand+Disease%22 on Mar. 6, 2008, 5 pgs.
Tsementzis, S.A, et al., "Fibrinolytic Activity After Subarachnoid Hemorrhage and the Effects of Tranexamic Acid," *Acta Neurochir. (Wien)*, vol. 103 (1990), pp. 116-121.
Turner, R. R., "Patient-Reported Outcomes: Instrument Development and Selection Issues," *ISPOR, Value in Health*, 2007; 10: sup. 2, S86-S93.
Van Den Akker, O., et al, "Pyscho physiological Responses in Women Reporting Severe Premenstrual Symptoms" *Psychosomatic Medicine* 51: 319-328 (1989).
van Eijkeran, M.A. et al, "Menorrhagia. Current Drug Treatment Concepts," *Drugs*. 1992; 43 (2) 201-209.
Varner, R. et al., "Medicine or Surgery (MS); a randomized clinical trial comparing hysterectomy and medical treatment in premenopausal women with abnormal bleeding", *Controlled Clinical Trials*, 25 (2004) 104-118.
Vemylen J., et al, "A Double blind study of the effect of tranexamic acid in essential menorrhagia." *Thromb. Diath. Haemorrh.*, Dec. 31, 1968; 20(3): 583-587.
Verstraete, M., "Clinical Application of Inhibitors if Fibrinolysis," *Drugs*, 29: 236-261 (1985).
Vilos, GA, et al, "Guidelines for the management of abnormal uterine bleeding" *J. Obstet. Gynaecol. Can.*, 2001; 23; 704-709.
Wallenstien, G., et al, "Development and Validation of the Premenstrual Symptoms Impact Survey (PMSIS): A disease-specific Quality of Life Assessment Tool," *Journal of Women's Health*, 2008; 17: No. 3.
Waltzman et al, "Effects of Tranexamic Acid on the Coagulation and Fibrinolytic Systems in Pregnancy Complicated by Placental Bleeding," *New Toxicology for Old Arch. Toxicol.*, Suppl. 5 (1982), pp. 214-220.
Ware, J.E., Jr. et al, "The MOS 36-Item Short-Form Health Survey (SF36)," *Med. Care*, 1992; 30: 473-483.
Warner, P.E. et al., "Menorrhagia I: Measured blood loss, clinical feathers, and outcome in women with heavy periods: A survey with follow-up data," *Am. J. Obstet. Gynecol.*, 2004; 190: 1216-23.
Warner, P.E., et al, "Menorrhagia II: Is the 80mL blood loss criterion useful in management of complaint of menorrhagia?" *Am. J. Obstet. Gynecol.*, 2004; 190: 1224-29.
Wellington et al, Tranexamic Acid, A Review of its Use in the Management of Menorrhagia Drugs, *Drugs* 63(13), p. 1417-1433, 2003.
Westrom, Lars, MD et al, "Effect of Tranexamic Acid (ACMCA) in Menorrhagia with Intrauterine Contraceptive Devices," *J. Reprod. Med.*, 1970; 5: No. 4.
Wiegel, M., et al., "The Female Sexual Function Index (FSFI): Cross Validation and Development of Clinical Cutoff Scores", *J Sex Martial Ther*. 2005, 31; 1-20.
Wilson et al., "Physiological Pharmaceutics Biological Barriers to Drug Absorption", Horwod Ellis, Chichester, Chapter 4, pp. 47-70 (1989).
Wilson, I, B., et al., "Linking Clinical Variables with Health Related Quality of Life: A conceptual model of Patient Outcomes", *J. Am. Med. Assoc.* 1995, 273(1), 59-65.
Winkler, U.H., "The effect of tranexamic acid on the quality of life of women with heavy menstrual bleeding," *Eur. J. Obstet. Gynecol. Reprod. Biol.*, 2001; 99: 238-243.
Working Party for Guidelines for the Management of Heavy Menstrual Bleeding. "An evidence-based guideline for the management of heavy menstrual bleeding," *NZ Med. J.*; 1999; 112: 174-7.
Wyrwich, K.W. et al., "Further Evidence Supporting an SEM-Based Criterion for Identifying Meaningful Intra-Individual Changes in health Related quality of Life", *J. Clin. Epidemiol.* 2; 861-873. vol. 52, (1999).
Wyrwich, K.W. et al., "Identifying meaningful intra-individual change standards for health related quality of life measures", *J. Eval. Clin. Pract.*, 2000, 6, 1, 39-49.
Wyrwich, K.W. et al , "Linking Clinical relevance and Statistical Significance in Evaluating Intra-Individual Changes in health Related quality of Life", *Med. Care* 1999 37 (5), 469-478.
Yikorkala, O., et al, "Comparison between antifibrinolytic and antiprostaglandin treatment in the reduction of increased menstrual blood loss in women with intrauterine contraceptive devices," *Brit. J. Obstet. Gynecol.*, 1983; 80: 87-83.
Zee, B.C., "Growth Curve model Analysis for Quality of Life Data", *Statist. Med.*, 17, 757-766 (1998).
Japanese Patent Application No. 2011-062281, Final Rejection dated Jan. 7, 2014.
U.S. Court of Appeals for the Federal Circuit, *Ferring B.V. v. Watson Laboratories, Inc.*, Appeal No. 2014-1377, Aug. 22, 2014, 17 pp.
U.S. Court of Appeals for the Federal Circuit, *Ferring B.V. v. Watson Laboratories, Inc.*, Appeal No. 2014-1416, Aug. 22, 2014, 19 pp.
U.S. Appl. No. 11/346,710, Office Action (Non-final) dated Jul. 14, 2014, 5 pp.
U.S. Appl. No. 12/770,185, Office Action (Final) dated Jun. 18, 2014, 10 pp.
U.S. Appl. No. 13/230,902, Office Action (Non-final) dated Jun. 17, 2014, 13 pp.
Bushnell et al., "Menorrhagia Impact Questionnaire: assessing the influence of heavy menstrual bleeding on quality of life," Curr. Med. Res. Opin., 2010, 26(12):2745-2755.
Evonik Industries, Brochure, "Eudragit® Acrylic polymers for solid oral dosage forms" Aug. 2012, 16 pp.
Attorney Timothy Kratz, Notification of Paragraph IV Certification Regarding U.S. Patent No. 8,487,005 Pursuant to Section 505(j)(2)(B)(i)-(ii) of Federal Food, Drug, and Cosmetic Act, dated Aug. 29, 2013, 31 pp.

(56) References Cited

OTHER PUBLICATIONS

Patel et al., "A comparative study of tranexamic acid and ethamsylate in menorrhagia," Int. J. Basic Clin. Pharmacol., 2012, 1(2):85-90.
Janet Vaughn, Director, Regulatory Affairs, Watson Laboratories Florida, Notification of Invalidity and/or Non-infringement for U.S. Patent No. 8,487,005 Pursuant to § 505(j)(2)B(iv) of the Federal Food, Drug, and Cosmetic Act, dated Jul. 23, 2013, 11 pp.
Office Action (non-final) dated Sep. 12, 2013 for U.S. Appl. No. 11/346,710, 13 pp.
Office Action (non-final) dated Oct. 18, 2013, for U.S. Appl. No. 12/770,185, 15 pp.
Office Action (non-final) dated Aug. 6, 2013 for U.S. Appl. No. 13/230,902, 31 pp.

* cited by examiner

Measure #1
During your most recent menstrual period, your blood loss was:
1. LIGHT  2. MODERATE  3. HEAVY  4. VERY HEAVY

Measure #2
During your most recent menstrual period, how much did your bleeding limit your work outside or inside the home?
1. NOT AT ALL  2. SLIGHTLY  3. MODERATELY
4. QUITE A BIT  5. EXTREMELY

Measure #4
During your most recent menstrual period, how much did you bleeding limit you in your social or leisure activities?
1. NOT AT ALL  2. SLIGHTLY  3. MODERATELY
4. QUITE A BIT  5. EXTREMELY

Measure #3
During your most recent menstrual period, how much did you bleeding limit you in your physical activities?
1. NOT AT ALL  2. SLIGHTLY  3. MODERATELY  4. QUITE A BIT
5. EXTREMELY

Measure #5
Please mark [X] all activities that were limited by bleeding during your recent menstrual period.
[ ] Walking       [ ] Shopping          [ ] Traveling /
[ ] Standing      [ ] Home Management       Vacation
[ ] Climbing Stairs  [ ] Leisure        [ ] Other? _____
[ ] Squatting or  [ ] Exercise          [ ] Other? _____
    bending down  [ ] Sports
[ ] Childcare     [ ] Gardening

Measure #6
Compared to your previous menstrual period, would you say your blood loss during this period was:
0. ABOUT THE SAME   1. BETTER (go to 6a)   2. WORSE (go to 6b)

Measure #6a
If you menstrual bleeding 'improved' since your last period, please indicate how much.
7. A VERY GREAT DEAL BETTER
6. A GREAT DEAL BETTER
5. A GOOD DEAL BETTER
4. AN AVERAGE AMOUNT BETTER
3. SOMEWHAT BETTER
2. A LITTLE BETTER
1. ALMOST THE SAME

Measure #6b
If you menstrual bleeding 'worsened' since your last period, please indicate how much.
7. A VERY GREAT DEAL WORSE
6. A GREAT DEAL WORSE
5. A GOOD DEAL WORSE
4. AN AVERAGE AMOUNT WORSE
3. SOMEWHAT WORSE
2. A LITTLE WORSE
1. ALMOST THE SAME, HARDLY WORSE AT ALL

Measure #6c
Was this a meaningful or important change for you?

0. NO          1. YES

FIG. 4

TRANEXAMIC ACID FORMULATIONS

RELATED APPLICATIONS

This application is a continuation of U.S. patent application Ser. No. 12/433,408 filed Apr. 30, 2009 which is a continuation-in-part of U.S. patent application Ser. No. 12/220,241, filed Jul. 23, 2008, which is a continuation of U.S. patent application Ser. No. 11/072,162, filed on Mar. 4, 2005, which claims priority from U.S. Provisional Application No. 60/550,113, filed Mar. 4, 2004, and U.S. Provisional Application No. 60/592,885, filed Jul. 30, 2004. The disclosures of each of these related applications are hereby incorporated by reference in their entireties.

FIELD OF THE INVENTION

The invention is directed to oral tranexamic acid formulations and methods of treatment with these formulations.

BACKGROUND OF THE INVENTION

Tranexamic acid (trans-4-(aminomethyl)cyclohexanecarboxylic acid, Cyldokapron® (Pfizer) is an antifibrinolytic agent. That is, it helps to prevent lysis or dissolution of a fibrin clot which foams in the normal physiologic process of hemostasis. Its mechanism of action is as a competitive inhibitor of plasminogen activation, and as a noncompetitive inhibitor of plasmin; both plasminogen and plasmin are activators of fibrinolysis and active clot-lysing agents. Tranexamic acid thus helps to stabilize fibrin clots, which in turn maintains coagulation and helps to control bleeding.

Tranexamic acid is used to control excess bleeding, for example, excess bleeding that occurs during dental procedures in hemophiliacs and for heavy bleeding during menstruation (menorrhagia). Women suffering from menorrhagia are typically treated orally with 500 mg tranexamic acid tablets administered three or four times daily with a total daily dose ranging from 3 grams/day (two tablets every eight hours) to 6 grams/day (three tablets every six hours). However, this treatment may cause adverse gastrointestinal reactions, including nausea, vomiting, diarrhea, and cramping, etc. These gastrointestinal side effects are due to the quantity of tranexamic acid and/or rapid rate of release of tranexamic acid into the stomach with each dose, as well as the large quantity of excipients used in the tablet formulation that are introduced into the stomach. Such side effects, in addition to the cramping, bloating, pain, and other symptoms mat may accompany menses, are undesirable, and a formulation of tranexamic acid is needed which will reduce or eliminate these side effects.

Menstrual Bleeding

Menstrual Bleeding disorders encompass a number of conditions including bleeding associated with uterine fibroids, endometriosis, or bleeding as a result of deficiencies in the clotting process for example, von-Willebrand's disease. Studies suggest that as many as 11% of the women who experience heavy menstrual bleeding, suffer from an inherited bleeding disorder such as von Willebrand's disease. Excessive Menstrual Bleeding is menstruation at relatively regular intervals but with excessive blood loss over the menses period which may be prolonged. Heavy Menstrual Bleeding (also referred to as "Menorrhagia") is a serious, persistent, and recurrent medical condition that is one of the most common complaints encountered by gynecologists and primary care physicians (Palep Singh, 2007). A 2005 survey of 273 obstetrician/gynecologists found that they see an average of 18 to 25 symptomatic patients per month. Heavy Menstrual Bleeding is a hyperfibrinolytic condition defined as cyclic, normal intervals of menstruation with excessive volume. Menorrhagia is often associated with a disruption in daily routines, work, and sexual activity leading to a significant decrease in health-related quality of life and time lost from work or school. While Menorrhagia is rarely life threatening, when undiagnosed and untreated, it may over time cause iron deficiency anemia and increased fatigue, both of which affect normal life activities, relationships, social activities, and various aspects of mental well-being (irritation, anxiety). Left untreated it may be associated with subsequent morbidity including dysmenorrhea, hospitalization, red blood cell transfusions and chronic pain. Annually, approximately 10% of women of reproductive age report Menorrhagia (Rees 1991; van Eijkeren, 1992) and according to the Center for Disease Control (CDC), 3 million women of reproductive age report Menorrhagia yearly, 60% of which have no known etiology. Studies report that as many as thirty percent of premenopausal women perceive their menses to be excessive.

Women suffering from menorrhagia often have greater uterine fibrinolytic activity man women with normal cyclic menstrual blood loss (MBL). High concentrations of plasminogen activators are found in both the uterus and menstrual fluid (Albrechtsen, 1956a,b). Rybo (1966) found significantly higher concentration of endometrial plasminogen activators in women with excessive menstrual bleeding compared to women with normal menstrual loss.

Causes of Menorrhagia include pelvic diseases (myomata [fibroids], adenomyosis or uterine polyps), intrauterine contraceptive devices, and systemic disorders (coagulopathies such as thrombocytopenia or von Willebrand's disease, and hypothyroidism). In contrast to menorrhagia, the term 'dysfunctional uterine bleeding' refers to excessive, prolonged or irregular bleeding from the endometrium that is unrelated to systemic disease (Wathen, 1995), and is usually associated with anovulation. Menorrhagia is also distinguished from other ovulatory bleeding disorders, such as metrorrhagia (intermenstrual bleeding), menometrorrhagia (irregular heavy menstrual bleeding) and polymenorrhea (menstrual cycle less than 21 days).

Diagnosis of Menstrual Blood Loss

In clinical trials, menstrual bipod loss (MBL) is usually determined by measuring the amount of hemoglobin recovered from sanitary products (hiring the menstrual cycle, using the alkaline hematin method (Fraser, 1994). However, it is important to remember that blood accounts for only about 50% of total menstrual flow, with endometrial transudate accounting for the remainder (Fraser, 1994). Total menstrual flow can be estimated by weighing of sanitary products or by comparisons with a pictorial blood loss assessment chart. However, the use of these quantitative and semi-quantitative methods is not practical in non-trial settings. Rather, the diagnosis of Menorrhagia in the healthcare clinic is made by medical providers on the basis of patient's perceived and self-reported medical history, routine laboratory assessments of the patient's general health status, and gynecological examinations.

Clinically heavy menstrual bleeding is sometimes defined as total blood loss exceeding about 80 ml per cycle or menses lasting longer than seven days. The volume lost however, varies widely. Clinically losses from about 30 ml to 60 ml, 60 to 80 ml, 80 to 100 ml, to as high as 1000 ml per cycle are observed. Menstrual blood losses of 50 to 60 ml are associated with a negative iron balance and iron deficiency anemia is diagnosed in about 67% of the women who lose an excess of 80 ml per day. Other criteria for diagnosing the condition include measuring the number and size of blood clots in the meneges, or monitoring the use of pads or tampons. It is estimated that perhaps only ten percent of women who perceive their loss to be excessive actually fall within the clinical definition. The 80 ml definition has been repeatedly questioned, and alternative definitions broadened the blood loss range used for patient evaluations.

Blood loss volume assessments commonly require the collection and preservation of menstrual pads or tampons, the extraction of the pads and the accurate measurement of the blood content. Women are instructed to collect all sanitary towels and tampons during the course of menstrual diagnosis period or the course of a clinical study period. Blood loss can be measured by extraction of the blood from the sanitary material with 5% sodium hydroxide followed with a spectrophotometric measurement of hematin at a wavelength of about 540 nm. The total blood loss can be calculated for an individual by comparison of the patients plasma blood hemoglobin measurement with the collected hemoglobin values.

The collection of the blood sample discourages the routine use of the test in the diagnosis or in the treatment of the condition. In die course of a routine visit with a physician other blood work may be appropriate but licks a casual relation to the heavy bleeding disorder. The battery of routine laboratory tests may include patient blood hemoglobin, haematocrit, platelet count, bilirubin, serum creatinine and serum ferritin. In sum, diagnosis in the routine course of practice relies heavily on the woman's perception of the volume of blood lost during menses.

Diagnosis and Treatment of Heavy Menstrual Bleeding Disorders (Menorrhagia)

A number of medical and surgical interventions are available to treat menstrual bleeding disorders. Currently available non-surgical treatments for heavy bleeding disorders, include, hormonal treatments (e.g., oral contraceptives), high-dose progestin therapy, desmopressin acetate, ethamsylate, nonsteroidal anti-inflammatory drugs (NSAIDs), the antifibrinolytic drugs aminocaproic acid and tranexamic acid. Even with the drug treatments available, surgery remains a common treatment.

Although not approved for menorrhagia in the US, use of oral contraceptives for menorrhagia is widely accepted. Oral contraceptives may not be a preferred therapy for some women because of age (younger females), unwanted side effects (nausea and vomiting, breakthrough bleeding, weight change, migraines and depression), and safety concerns (increased risk of thromboembolism, stroke, myocardial infarction, hepatic neoplasia and gall bladder disease). High-dose progestin (synthetic versions of the hormone progesterone) may also be given to women with menorrhagia, either orally or by a progestin-releasing device inserted into the uterus (intrauterine device). Side effects include nausea, bloating, mood changes, and breast tenderness.

Although it is typically a last resort, desmopressin acetate is sometimes used to help lighten menstrual flow in women with menorrhagia. The effectiveness of desmopressin is thought to vary between individuals. Side effects include headache, tachycardia, facial flushing, and rare reports of thromboembolism.

NSAIDs are sometimes used to treat menorrhagia as they may reduce blood flow while providing analgesia for pain associated with the condition (Shaw, 1994). Side effects associated with chronic NSAID use include gastrointestinal bleeding, ulceration, and perforation; and renal effects such as hyperkalemia, hyponatremia, acute renal insufficiency, interstitial nephritis, and renal papillary necrosis.

Hysterectomy or endometrial resection are options if other forms of therapy are not effective or are unsuitable for some reason. Possible surgical complications include infection, uterine perforation, and other complications associated with major surgery.

Antifibrinolytic drugs, such as $\epsilon$-aminocaproic acid and tranexamic acid (immediate-release formulation) have been used to treat HMB in women with or without a diagnosed bleeding disorder (van Eijkeren, 1992; Bonnar, 1996; Vermylen, 1968; Nilsson, 1965). The available evidence from published literature suggests that tranexamic acid at doses of ~4 g/day (typically 1 g every 6 hours) is effective in the treatment of HMB and is associated with few side effects (Callender, 1970; Dunn, 1999; Edlund, 1995; Preston, 1995). In Sweden, the average dose of tranexamic acid to treat HMB is 35 g/day (Rybo, 1991). Thus, tranexamic acid is used extensively in Europe, Canada, Asia, Japan, Australia and New Zealand to treat menorrhagia, but is not approved for this indication in the US.

Tranexamic acid is a competitive inhibitor of plasminogen activation (see review by Dunn, 1999). Binding of tranexamic acid to plasminogen does not prevent conversion of plasminogen to plasmin by tissue plasminogen activator, but the resulting plasmin/tranexamic acid complex is unable to bind to fibrin. Thus, enzymatic breakdown of fibrin by plasmin (fibrinolysis) is inhibited. At higher concentrations, tranexamic acid is also a noncompetitive inhibitor of plasmin.

Before medical and surgical interventions can be initiated, diagnosis of a heavy menstrual bleeding disorder must be accomplished.

Diagnosis and treatment of disease often depends on the patient's perception and subsequent description of symptoms, the physician's evaluation of the patient's description, the physician observations of the patient and laboratory test results. Menstrual bleeding disorders do not lend themselves to physician observation or to routine laboratory testing. Patient observations and the physician's evaluation of the patient's description are subjective and thus variable. In addition a women's medical history has been found to be a poor predictor of menstrual blood loss. Neither the duration of menses nor the number of sanitary pads worn accurately corresponds to the woman's actual menstrual blood loss (Chimbira, Haynes, year). An objective assessment of blood loss using the alkaline haematin assay has been shown to be reproducible but it is not suited for routine clinical use by healthcare providers. To date no effective instrument for reliably diagnosing and/or monitoring the treatment of menstrual bleeding disorders has been developed despite the significant number of women who suffer from these conditions.

Previously, studies have focused on the impact of symptoms of bleeding disorders on patients' health related quality of life. As the effects of menstrual bleeding disorders are primarily symptomatic, the subjective outcome namely symptom alleviation, cannot be objectively measured. In research from European countries where the antifibrinolytic drug tranexamic acid is currently available, treatment with this antifibrinolytic has reduced heavy menstrual bleeding by 40-50% and unproved the health-related quality of life of affected women on measures of social activity. Work performance, productivity, cleanliness, overall functioning and tiredness.

Jenkinson et al, Quality in Health Care 1996; 5; 9-12 evaluated the validity and internal reliability of the short form-36 (SF36) health survey questionnaire in women presenting with menorrhagia. The study concluded that several questions on the questionnaire were difficult to answer for patients with heavy menstrual bleeding. Such problems were suggested as possible interferences with the validity of the measure. Jenkinson warns that because a subjective measure works well in, one population with one group, this cannot be taken to imply its appropriateness for all groups or conditions.

Edlund, in an abstract from a seminar on Dysfunctional Uterine Bleeding, Feb. 23, 1994, indicates that a questionnaire was used in a Swedish study of 2205 women who described their menstruation as excessive.

Winkler in a study based in part on the Edlund work, concluded that the treatment of heavy menstrual bleeding with tranexamic acid increased the quality of life of the treated patients. The Winkler study was an open label uncontrolled usage study which included 849 patients. A questionnaire was used prior to treatment and after the first and third menstruation. The study indicates that 80% of the women were satisfied with the treatment. The questionnaire used a series of eight question combined with an assessment by the patients of the change in quantity of menstrual flow.

Ruta, D. A., Quality of Life Research, 4, (33-40), 1995 finds that menorrhagia is a common problem in gynecological practice and that women seek professional help primarily because of the deleterious effect on their quality of life. Ruta recognizing the importance of evaluating the effectiveness of the treatments developed a questionnaire based on the type of questions frequently asked when taking a gynecological history. A series of questions were devised which assessed fifteen factors including the duration of the period, the regularity of the period, pain, problems with soiling/staining, interference with work, interference with leisure. Ruta concluded that the clinical questionnaire may be useful in selecting patients for hysterectomy and assessing the outcome of conservative treatment especially in combination with the SF-36 questionnaire.

Diagnostic Test for Menstrual Bleeding

The alkaline haematine test described above provides quantitative assessments of the extent of menstrual bleeding. This test allows the physician to diagnose and monitor the progress of a women's menstrual process. However the test is impractical and difficult to perform. The test requires women to capture used menstrual pads over the course of her period, preserve the samples in a condition such that the blood content within the pad may be accurately extracted and quantitated. Requesting a patient to perform menses sample collection may be practical in the course of a clinical trial where procedures are specified and monitored however, in routine medical practice, the use of such a test procedure to diagnose and monitor a women's menstrual bleeding is impractical and the data generated is unreliable.

The need remains to develop an assessment system which replaces previously studied diagnostic techniques and the alkaline haematine test and provides a reliable measure of both the occurrence of the disorder and the progress of the disorder. The present invention fills this need by providing a Heavy Menstrual Bleeding Instrument (HMBI) which is capable, of diagnosing, and monitoring the treatment of a patient with a menstrual bleeding disorder.

There also remains a need to provide Heavy Menstrual Bleeding (HMB) therapy that is safe, efficacious and only administered (hiring the monthly period of heavy menstruation, addresses the excessive fibrinolysis implicated in many causes of menorrhagia, and fills a currently recognized unmet medical heed in the US. Therapy for HMB is expected to reduce the incidence and extent of iron-deficiency anemia, and to provide a nonhormonal medical therapy option in lieu of the numerous invasive procedures (e.g., transcervical endometrial resection) and major surgery (hysterectomy) performed annually.

SUMMARY OF THE INVENTION

It is an object of the invention to provide an oral dosage form comprising tranexamic acid which is suitable for oral administration on a two or three times a day basis to humans.

It is a further, object of certain embodiments of the invention to provide a method of treating a patient in need of tranexamic acid therapy with one or more oral dosage forms comprising tranexamic acid.

It is a further object of certain embodiments of the present invention to provide a method of treating a patient suffering from heavy menstrual bleeding (menorrhagia) by orally administering to the patient one or more dosage forms comprising tranexamic acid which provide(s) for therapeutically effective levels of tranexamic acid suitable for two or three times a day administration.

It is a further object certain embodiments of the invention to provide a formulation comprising an amount of tranexamic acid which when released in the gastric contents provides fewer adverse effects than with certain current tranexamic acid therapy.

The above advantages and objects and others can be achieved by virtue of the present invention which is directed in part to a method of treating a patient in need of tranexamic acid therapy comprising administering to the patient about 1300 mg of tranexamic acid or pharmaceutically acceptable salt thereof in one or more oral dosage forms including the tranexamic acid or pharmaceutically acceptable salt thereof such that the dose administered provides a mean maximum plasma concentration ($C_{max}$) of tranexamic acid of from about 9 to about 15 mcg/ml preferably from about 10 to about 14 mcg/ml, more preferably about 12 mcg/ml after single dose oral administration to humans.

In certain embodiments, the invention is directed to an oral dosage form comprising 650 mg of tranexamic acid or pharmaceutically acceptable salt thereof which provides a mean maximum plasma concentration ($C_{max}$) of tranexamic acid of from about 9 to about 15 mcg/ml, preferably from about 10 to about 14 mcg/ml, more preferably about 12 mcg/ml per 1300 mg of tranexamic acid after single dose oral administration to humans.

In certain embodiments, the invention is directed to an oral dosage form comprising 650 mg of tranexamic acid or pharmaceutically acceptable salt thereof which provides a mean $T_{max}$ of tranexamic acid at from about 2 to about 4 hours, preferably at about 3 hours after oral administration to humans.

In certain embodiments, the invention is directed to an oral dosage form comprising about 650 mg of tranexamic acid or pharmaceutically acceptable salt thereof and a pharmaceutically acceptable excipient; said dosage form providing an in-vitro dissolution release rate of the tranexamic acid, when measured by a USP 27 Apparatus Type II Paddle Method @ 50 RPM in 900 ml water at 37±0.5° C., of at least about 70% by weight tranexamic acid or pharmaceutically acceptable salt thereof or released at about 45 minutes, and preferably 100% by weight tranexamic acid or pharmaceutically acceptable salt thereof release by about 45 minutes.

In certain embodiments, the invention is directed to an oral dosage form comprising about 650 mg of tranexamic acid or pharmaceutically acceptable salt thereof and a pharmaceutically acceptable excipient, said dosage form providing an in-vitro dissolution release rate of the tranexamic acid or pharmaceutically acceptable salt thereof from the dosage form, when measured by the USP 27 Apparatus Type II Paddle Method @ 50 RPM in 900 ml water at 37±0.5° C. of about 0% to about 95% by weight tranexamic acid or pharmaceutically acceptable salt thereof released at about 15 minute, from about 30% to about 100% by weight tranexamic acid or pharmaceutically acceptable salt thereof released at about 30 minutes, from about 70% to about 100% by weight tranexamic acid or pharmaceutically acceptable salt thereof released at about 45 minutes, about 100% by weight tranexamic acid or pharmaceutically acceptable salt thereof released at about 60 minutes.

In certain embodiments, the invention is directed to an oral dosage form comprising about 650 mg of tranexamic acid or pharmaceutically acceptable salt thereof and a pharmaceutically acceptable excipient, said dosage form providing an in-vitro dissolution release rate of the tranexamic acid or pharmaceutically acceptable salt thereof from the dosage form, when measured by the USP 27 Apparatus Type II Paddle Method @ 50 RPM in 900 ml water at 37±0.5° C. of about 50% to about 95% by weight tranexamic acid or pharmaceutically acceptable salt thereof released at about 15 minutes, from about 70% to about 100% by weight tranexamic acid or pharmaceutically acceptable salt thereof released at about 30 minutes, from about 80% to about 100% by weight tranexamic acid or pharmaceutically acceptable salt thereof released at about 45 minutes, about 100% by weight tranexamic acid or pharmaceutically acceptable salt thereof released at about 60 minutes.

In certain embodiments, the invention is further directed to an oral dosage form comprising tranexamic acid (preferably in an amount of about 650 mg) or pharmaceutically acceptable salt thereof and a pharmaceutically acceptable excipient, which provides for a bioavailability of tranexamic acid of greater than 40%, from about 41% to about 60%, preferably from about 42% to about 50%, more preferably about 46% after oral administration to humans.

In certain embodiments, the invention is further directed to an oral dosage form comprising about 650 mg of tranexamic acid or pharmaceutically acceptable salt thereof and a pharmaceutically acceptable excipient, the dosage form being suitable for oral administration on a twice a day basis, and the dosage form providing a mean maximum plasma concentration ($C_{max}$) of tranexamic acid of from about 13.5 to about 22.5 mcg/ml, preferably from about 15 to about 21 mcg/ml, more preferably about 18 mcg/ml per 1950 mg tranexamic acid after single dose oral administration to humans.

In certain embodiments, the invention is further directed to a method of treating a patient with a therapeutically effective amount of tranexamic acid or pharmaceutically acceptable salt thereof comprising administering to the patient two or three dosage forms of the present, invention, each dosage form comprising from about 585 mg to about 715 mg of tranexamic acid or pharmaceutically acceptable salt thereof, preferably about 650 mg tranexamic acid or pharmaceutically acceptable salt thereof, and a pharmaceutically acceptable excipient.

In certain embodiments, the invention is directed to a dose of tranexamic acid or pharmaceutically acceptable salt thereof comprising two oral dosage forms, each oral dosage form comprising from about 585 mg to about 715 mg, preferably about 650 mg of tranexamic acid or pharmaceutically acceptable salt thereof, and a pharmaceutically acceptable excipient, the dose providing a therapeutic effect when administered three times a day.

In certain embodiments, the invention is directed to a dose of tranexamic acid or pharmaceutically acceptable salt thereof comprising three oral dosage forms, each oral dosage form comprising from about 585 mg to about 715 mg, preferably about 650 mg of tranexamic acid or pharmaceutically acceptable salt thereof, and a pharmaceutically acceptable excipient, the dose providing a therapeutic effect when administered twice, a day.

in certain preferred embodiments, the oral dosage form of the invention further provides a mean transit time of said tranexamic acid of 7.21±1.01 hours when administered across a patient population.

In certain preferred embodiments, the oral dosage form of the invention further provides a mean absorption time of said tranexamic acid of 3.70±0.94 hours when administered across a patient population.

In certain embodiments, the invention is further directed to an oral dosage form comprising tranexamic acid or pharmaceutically acceptable salt thereof and at least one pharmaceutically acceptable excipient which provides less than about 20 percent incidence of nausea, less than about 15 percent incidence of nausea, preferably less than about 10 percent incidence of nausea as a side effect after single dose oral administration across a patient population.

In certain embodiments the dosage form provides less CNS side effects (e.g., headache), less GI side effects (e.g., nausea), or combination thereof in comparison to a therapeutically equivalent amount of tranexamic acid administered intravenously in five minutes or less when administered across a patient population.

In certain preferred embodiments, the therapeutically effective dose of the tranexamic acid is provided via the administration of two or more dosage units. For example, if the dosage unit comprises 650 mg of tranexamic acid and the dose for administration is about 1300 mg then two dosage units would be administered to a patient in need of such treatment, or for example, when the dose for administration is 1950 mg, three dosage units would be administered.

In certain preferred embodiments, the invention is further directed to a method of treating a patient with one or more oral dosage forms comprising tranexamic acid or pharmaceutically acceptable salt thereof and a pharmaceutically acceptable excipient, wherein the oral dosage form provides a therapeutically effective plasma level of tranexamic acid in accordance with a three times a day (TID) dosing schedule, and the therapeutically effective dose administered comprises about 1300 mg of tranexamic acid.

In certain preferred embodiments, the invention is further directed to a method of treating a patient with one or more oral dosage forms comprising tranexamic acid or pharmaceutically acceptable salt thereof and a pharmaceutically acceptable excipient, wherein the oral dosage form provides a therapeutically effective plasma level of tranexamic acid in accordance with a twice a day (BID) dosing schedule, and the therapeutically effective dose administered comprises about 1950 mg of tranexamic acid.

In certain embodiments, the tranexamic acid for use in the methods and formulations of the present invention is in the form of a pharmaceutically acceptable salt thereof. Such salt forms include for example and without limitation the sodium salt, potassium salt, calcium salt, magnesium salt and the like; as well as the hydrochloride, hydrobromide, sulfate, phosphate, formate, acetate, trifluoroacetate, maleate, tartrate, methanesulfonate, benzenesulfonate, p-toluenesulfonate-methanesulfonate salt forms, and the like. Preferably the active ingredient for use in accordance with the present invention is tranexamic acid.

The term "$C_{max}$" unless otherwise indicated is meant for purposes of the present invention to mean the maximum plasma concentration of a medicament achieved after single dose administration of a dosage form, or the maximum plasma concentration of a medicament achieved over a dosing interval from multiple-doses at steady-state in accordance with the present invention.

The term "$T_{max}$" is meant for purposes of the present invention to mean the elapsed time from administration of a dosage form to the time the $C_{max}$ of the medicament is achieved.

The term "steady state" means mat the amount of me drug reaching the system is approximately the same as the amount of the drug leaving the system. Thus, at "steady-state", the patient's body eliminates the drug at approximately the same rate that the drug becomes available to the patient's system through absorption into the blood stream.

The term "mean" for purposes of the present invention, when used to define a pharmacokinetic value (e.g., $T_{max}$), unless specified otherwise, represents the arithmetic mean value measured across a patient or subject population.

The term "three times a day (TID) basis" for purposes of the present invention, means that the dosage regimen is to be administered three times a day, preferably on a schedule of every 8 hours.

The term "mean transit time" is understood by those skilled in the art and means the time-point where 63.2% of the total AUC is attained after oral administration, or 63.2% of the IV dose is eliminated, as described in *Applied Pharmacokinetics, Principles of Therapeutic Drug Monitoring*, Second Edition (1986), edited by William E. Evans, et al., the disclosure of which is hereby incorporated by reference in its entirety.

The term "mean absorption time" is understood by those skilled in the art and means a quantitative parameter which summarizes how long, on average, the drug molecule remains unabsorbed, i.e. persists in its dosage form and GI tract, also as described in *Applied Pharmacokinetics, Principles of Therapeutic Drug Monitoring*, Second Edition (1986), edited by William E. Evans, et al. Its value is not affected like the drug's absorption rate constants (ka), which can be skewed, due to incomplete release of drug from its dosage form, irregular absorption, lag-time, mixed, zero-order dissolution rates, changing GI motility, GI blood flow, first-pass effect, etc.

"Therapy" for excessive menstrual bleeding is defined for the purpose of this invention as one or more courses of treatment with an antifibrinolytic agent such as, but not limited to, tranexamic acid, aminocaproic acid, and any pharmaceutically acceptable salts, esters, derivatives, pro-drugs, metabolites; and analogues of any of the foregoing antifibrinolytic agents.

The term "heavy menstrual bleeding" is defined for purposes of the present invention as a perceived blood loss of at least heavy to very heavy which may correspond to a periodic blood loss of at least about 30 ml per cycle to as much as 1000 ml per cycle as measured by the alkaline hematin test. The periodic blood loss perceived or as measured with the alkaline hematin test may vary depending on the severity of the condition and the physiological make up of the individual patient. Therefore, heavy menstrual bleeding may include periodic blood losses of at least about 30 ml per cycle. Losses from between about 30 ml, about 40 ml, about 50 ml, about 60 ml, about 70 ml, about 80 ml, about 90 ml to about 300 ml are contemplated as are losses greater than 300 ml, such as for example, losses between about 300 ml to about 1000 ml.

BRIEF DESCRIPTION OF THE FIGURES

FIG. 4 is a listing of the Menorrhagia Impact Measures of the present invention.

DETAILED DESCRIPTION

Figure 1:
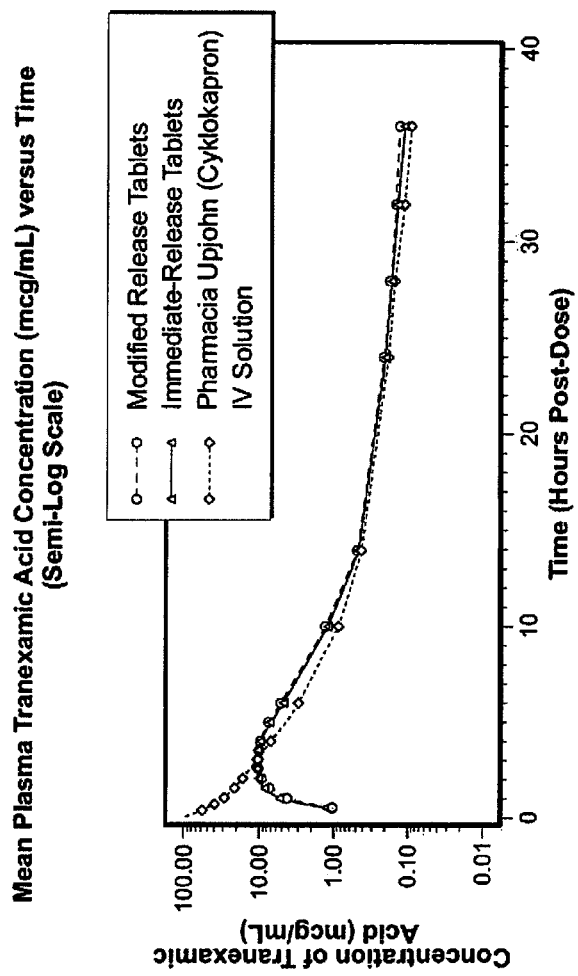
FIG. 1 depicts mean plasma concentration-time profiles on a semi-log scale over 36 hours for the formulations of Examples 1 and 2 compared to IV tranexamic acid (Cyklokapron).

The tranexamic acid (API) utilized in the formulations of the present invention is available from various manufacturers. The tranexamic add particles utilized in die present invention may range from about 0.1 to about 550 microns. For example, the tranexamic acid particles may have a particle size range from <about 0.5 to about 520 microns.

The tranexamic acid particles utilized in the present invention may have a $D_{25}$ particle size distribution ranging from about 5 to about 15 microns, a $D_{50}$ particle size distribution ranging from about 14 to about 73 microns, and a $D_{75}$ particle size distribution ranging, from about 30 to about 205 microns.

The particle size of the tranexamic acid utilized may also have a particle size range wherein about 1% of the particles are of a size greater than about 250 microns, about 8% of the particles are of a size of about 180 microns, about 9% of the particles are of a size of about 150 microns, about 4% of the particles are of a size of about 125 microns, about 20% of the particles are of a size of about 75 microns, about 14% of the particles are of a particle size of about 45 microns, and about 44% of the particles are of a particle size less than about 45 microns.

The tranexamic acid utilized may also have a particle size range wherein about 5% of the particles are of a size greater than about 250 microns, about 12% of the particles are of a size of about 180 microns, about 14% of the particles are of a size of about 150 microns, about 14% of the parades are of a size of about 125 microns, about 29% of the particles are of a size of about 75 microns, about 12% of the particles are of a particle size of about 45 microns, and about 14% of the particles are of a particle size less than about 45 microns.

The tranexamic acid utilized may also have a particle size range wherein about 2% of the particles are of a size greater, than about 250 microns, about 7% of the particles are of a size of about 180 microns, about 9% of the particles are of a size of about 150 microns, about 4% of the particles are of a size of about 125 microns, about 20.5% of the particles are of a size of about 75 microns, about 16% of the particles are of a particle size of about 45 microns, and about 41.5% of the particles are of a particle size less than about 45 microns.

The tranexamic acid utilized may also have a particle size range wherein about 0% of the particles are of a size greater than about 250 microns, about 5% of the particles are of a size of about 180 microns, about 12% of the particles are of a size of about 150 microns, about 11% of the particles are of a size of about 125 microns, about 31% of the particles are of a size of about 75 microns, about 17% of the particles are of a particle size of about 45 microns, and about 24% of the particles are of a particle size less than about 45 microns.

The tranexamic acid utilized may also have a particle size range wherein about 20% of the particles are of a size of about 125 microns, about 20% of the particles are of a size of about 75 microns, about 20% of the panicles are of a particle size of about 45 microns, and about 45% of the particles are of a particle size less than about 45 microns.

The dosage regimen typically listed for tranexamic acid in HMB (Heavy Menstrual Bleeding) therapy is 1-1.5 g per dose administered three-four times a day at the onset of copious menstrual bleeding and continued for the first 3-5 days of the menstrual cycle. However, the most frequently reported dosage regimen of tranexamic acid is an immediate release oral formulation in which 1 g tranexamic acid is administered four times a day (4 g per day) for HMB therapy outside of the US. Knowledge of this common regimen is supported by a careful review of the randomized controlled trials published in the medical literature, product labeling from other countries' regulatory authorities having the product approved for HMB therapy, utilization data from Sweden (Rybo 1991), correspondence and interviews with non-US clinicians having experience with the product. That regimen is currently the dosage being studied by the US Center for Disease Control (CDC) in women with HMB associated with bleeding disorders.

The absolute bioavailability of tranexamic acid observed when administering the European commercial formulation (Cyklokapron, KAbi AB, Sweden Batch 90288; assay 499 mgm/tablet) to male subjects is approximately 35% and its elimination correlates with renal creatinine clearance. Peak serum tranexamic acid concentrations occur approximately 3 hours after the oral administration of a European immediate-release tablet formulation (>85% dissolved at 15 minutes) (Pilbrant, et al. *Eur. J. Clin. Pharmacol.* (1981) 20:65-72). By comparison, the in vivo absorption profile observed with the European immediate-release formulation is slow and very gradual over 3 hours. Specifically, tranexamic acid serum concentrations are 9, 41, 73, 88 percent (with food), and 22, 63, 85, and 98 percent (lasting) of mammal absorption at 0.5, 1, 1.5 and 2 hours after a 2 g oral dose, respectively. Although not wishing to be held to any specific theory, it is presently hypothesized that tranexamic acid oral absorption appears to be controlled by a non-dissolution rate limited process, i.e. the rate and extent of oral absorption is a function of a trans-membrane passage-limited process, in order to explain the disparity between the time of product dissolution and relatively prolonged tmax (time to achieve the peak serum concentration).

Preferably, the goal of the formulation, dose strength and dosage regimen of the invention, is to provide HMB therapy which achieves from about 20% to 100% reduction in menstrual blood loss per menstrual cycle.

In accordance with the present invention an oral dosage form comprising about 650 mg of tranexamic acid is disclosed. Preferably, the oral dosage form contains at least one pharmaceutically acceptable excipient.

In certain embodiments, the oral dosage form of the present invention provides for an increased bioavailability as compared to other immediate release oral dosage forms currently available (e.g., Cyklokapron). In certain preferred embodiments the increased bioavailability allows therapeutic plasma levels of tranexamic acid to be reached with a lower dose of drug. Preferably, the increased bioavailability also decreases the amount of tranexamic acid that remains unabsorbed in the gastrointestinal which leads to decreased incidence of side effects that are typically associated with formulations that provide higher levels of unabsorbed tranexamic acid and prolonged exposure of the gastrointestinal tract to the higher tranexamic acid levels. Preferably the oral dosage form of the present invention provides for a bioavailability of tranexamic acid of greater than 40%, from about 41% to about 60%, preferably from about 42% to about 50%, more preferably about 46% after oral administration to humans.

In certain embodiments, the tranexamic acid included in the dosage form is from about 520 mg to about 1500 mg, preferably from about 520 mg to about 1000 mg. In one embodiment, the dose of tranexamic acid per tablet is in the range of about 520 mg to about 1000 mg for tablets and from about 520 mg to about 1500 mg for a sachet filled with granules. In another embodiment, the dose of tranexamic acid is in the range of about 3 grams/day to about 6 grams/day in three or four divided doses. As an example, a total dairy dose of 3 grams tranexamic acid may be divided into three doses of one tablet each with each tablet containing 1 gram tranexamic acid, or may be divided into four doses of one tablet each with each tablet containing 0.75 gram tranexamic acid. As another example, a total daily dose of 4 gram tranexamic acid may be divided into three doses of two tablets at each dose with each tablet containing 0.666 gram tranexamic acid, or may be divided into four doses of one tablet each with each tablet containing 1 gram tranexamic acid. As another example, a total daily dose of 5 gram tranexamic acid may be divided into three doses of one tablet each with each tablet containing 1.66 gram tranexamic acid, or may be divided into four doses of two tablets each with each tablet containing 0.625 gram tranexamic acid. As another example, a total daily dose of 6 gram tranexamic add may be divided into three doses of two tablets each with each tablet containing 1 gram tranexamic add; or may be divided into four doses of two tablets each with each tablet containing 0.75 gram tranexamic acid. For ease of swallowing, die dose of tranexamic acid taken at each dosing time may be delivered by taking multiple tablets. For example, the 4 gram daily dose may be delivered by taking two 666.67 mg tablets three times a day. Similarly, the 3 gram dairy dose may be achieved by taking two 550 mg tablets three times a day. Additionally, a1.95 g. gram daily dose may be achieved by taking three 650 mg tablets a day. Alternatively, for ease of reference, a dose of 600 mg, 650 mg, or 700 mg of tranexamic acid per tablet may be used, ma preferred embodiment, a total dairy dose of 3900 mg/day is administered in three divided doses of 1300 mg of two tablets at each dose with each tablet containing 650 mg of tranexamic add. Alternatively, each dose may be delivered by taking granules containing the prescribed amount of tranexamic acid presented in a convenient unit dose package. Such examples are not limiting and other doses within these ranges will be appreciated by those skilled in the art.

Since tranexamic add is primarily eliminated via the kidneys by glomerular filtration with more than 95% excreted unchanged drug in the urine, dosage adjustment may be recommended. The table below lists some recommended dosage adjustments for renal impairment:

| Serum Creatinine (mg/dl) | Estimated GFR* (ml/min) | Adjusted dose | Total daily dose |
|---|---|---|---|
| 1.4 to 2.8 | 30-60 | 1.3 g (two 650 mg tablets) BID | 2.6 g |
| 2.8 to 5.7 | 15-30 | 1.3 g (two 650 mg tablets) QD | 1.3 g |
| >5.7 | <15 | 1.3 g (two 650 mg tablets) every 48 hours or 650 mg (one tablet) every 24 hours | 0.65 g |

In certain embodiments, the invention is directed to a method of providing a tranexamic acid plasma concentration within the range of about 5 mcg/mL to about 15 mcg/mL by administration of at least one formulation of the present invention comprising tranexamic acid and pharmaceutically acceptable excipient on a three times a day basis to a patient in need of tranexamic acid treatment.

In certain embodiments, the invention is further directed to a method of treating a human patient with heavy menstrual bleeding (e.g., menorrhagia) comprising administering about 1300 mg of tranexamic acid on a three times a day basis to the human patient to provide a tranexamic acid plasma concentration within the range, of about 5 mcg/mL to about 15 mcg/mL after steady state oral administration to a human patient.

In certain embodiments, the invention is directed to a method of treating a patient suffering from menorrhagia, including patients with heavy menstrual bleeding due to fibroids, conization of the cervix, epistaxis, hyphema, hereditary angioneurotic edema, a patient with a blood coagulation disorder undergoing dental surgery, combinations thereof, and the like, by administering at least one dosage form of the present invention to the patient in need in tranexamic acid therapy.

In certain embodiments, the invention is directed to a method of treating heavy menstrual bleeding with a therapeutically effective dose of at least one oral formulation of the present invention comprising tranexamic acid and a pharmaceutically acceptable excipient wherein the menstrual blood loss per menstrual cycle is reduced by at least about 10 ml preferably at least about 20 ml, more preferably at least about 40 ml. In a most preferred embodiment the menstrual blood loss per menstrual cycle is reduced by greater than or equal to about 50 ml.

In certain embodiments, the invention is directed to a method of treating heavy menstrual bleeding with a therapeutically effective dose of at least one oral formulation of the present invention comprising tranexamic acid and a pharmaceutically acceptable excipient which upon oral administration to a human female reduces the blood loss per menstrual cycle by about 35 ml to about 200 ml, preferably about 40 ml to about 175 ml, more preferably from about 50 ml to about 150 ml.

In certain embodiments, the invention is further directed to a method of treating heavy menstrual bleeding with a therapeutically effective dose of at least one oral formulation of the present invention comprising tranexamic acid and a pharmaceutically acceptable excipient which upon oral administration to a human female reduces the blood loss per menstrual cycle by about 20% to 100%, preferably from about 20% to about 70%.

The menstrual blood loss can be measured by procedures known in the art. For example, in certain embodiments, the menstrual blood loss can be determined by a procedure described by (i) L. Hallbert, et al. in "Determination of Menstrual Blood Loss", *Scandinav J. Clin. & Lab Investigation*, 244-248, 16, 1964, wherein the procedure is performed by extracting the menstrual blood from vaginal tampons and towels with a sodium hydroxide solution, converting heme chromogens to alkaline hematin, which is determined spectrophotometrically; or (ii) the menstrual blood loss can be determined by a procedure described by J. Newton, M. D., et al., in "A Rapid Method for Measuring Menstrual Blood Loss Using Automatic Extraction", *Contraception,* 269-282, September 1977, Vol. 16, No. 3, wherein the procedure is based upon the formation of alkaline haematin after the blood has been extracted from vaginal tampons and sanitary towels by an automatic Stomacher Lab-Blender. The disclosures of the aforementioned articles are hereby incorporated by reference in then entireties.

The oral dosage forms of the present invention may be prepared as tablets, capsules, granules, pellets, powders, pellets, dragees, troches, non-pariels, pills or encapsulated suspension, and may be packaged into capsules, sachets, etc.

Tranexamic acid oral, dosage forms of the present invention are formulated to provide about a 650 mg dose of tranexamic acid. Typically, two oral dosage forms are administered to a patient in need of tranexamic acid therapy to provide a total dose of about 1300 mg. In addition, at least one pharmaceutically acceptable excipient is included in the oral dosage form. The pharmaceutically acceptable excipient may include, for example and without limitation, preservatives, diluents (e.g., microcrystalline cellulose), lubricants (e.g., stearic acid, magnesium stearate, and the like), binders (e.g., povidone, starch, and the like), disintegrants (e.g., croscarmellose sodium, corn starch, and the like), glidants (e.g., talc, colloidal silicon dioxide, and the like), granulating aids, colorants, and flavorants that are conventional in the pharmaceutical art. Specific examples of pharmaceutically acceptable excipients that may be used to formulate oral dosage forms are described in the Handbook of Pharmaceutical Excipients, American Pharmaceutical Association (2003), incorporated by reference herein.

Examples of diluents include dextrose, sucrose, starch, powdered cellulose, lactose, mannitol, microcrystalline cellulose, combinations thereof, and the like.

Examples of lubricants include magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, zinc stearate, combinations thereof and the like.

Examples of disintegrants include crospovidone, alginates, cellulose and its derivatives, clays, polyvinylpyrrolidone, polysaccharides, such as corn and potato starch, dextrins, croscarmellose sodium, sugars, combinations thereof, and the like.

Binders, when added to the formulation, promote granulation and/or promote cohesive compact during the direct compression into tablets. Examples of binders include povidone, acacia, cellulose derivatives, gelatin, glucose, polyvinylpyrrolidone, sodium alginate and alginate derivatives, sorbitol, starch, combinations thereof, and the like.

As used herein, alleviation of adverse effects using these formulations indicates any relief in one or more symptoms, such as decrease in incidence, severity, or duration of symptoms, and is not limited to absence of symptoms or elimination of symptoms. Thus, treatment includes any decrease in incidence, duration, intensity, frequency, etc. of adverse gastrointestinal symptoms including, but not limited to, headache, nausea, vomiting, diarrhea, constipation, cramping, bloating, and combinations thereof. The formulations may reduce symptoms at any time during tranexamic acid therapy, but minimized adverse effects are particularly noted immediately or shortly after dosing, that is, within the first few hours after dosing. As used herein, adverse gastrointestinal effects and side effects are used interchangeably to indicate nontherapeutic effects (i.e., not relating to any possible beneficial effects due to tranexamic acid), ranging from unpleasant but tolerable sensations to severe gastrointestinal symptoms. As used herein, the terms oral formulations, ingestible formulations, and orally administered formulations are used interchangeably and include any dosage forms which are ingested by mouth, including, but not limited to, tablets, pills, liquids, gelcaps, dragees, capsules, powders, granules, pellets, etc.

In certain embodiments, the formulation includes tranexamic acid in the range of about 50% by weight to about 95% or more by weight of the formulation. In other embodiments, tranexamic acid is in the range of about 60% by weight to about 90% by weight, or about 60% by weight to about 80% by weight of the formulation. The remaining weight may be made up of the pharmaceutically acceptable excipient.

To prepare formulations of the present invention, the pharmaceutically acceptable excipient may be incorporated into e.g., a tablet matrix with the tranexamic acid or coated onto e.g., the tranexamic acid or both. In certain embodiments, tablet formulations are formulated by granulating a blend of powders of the pharmaceutically acceptable excipient and the tranexamic acid. The powder blend is formed by combining portions of the powdered components that make up the tablet. These powders are intimately mixed by dry-blending. The dry blended mixture is granulated by wet mining of a solution of a binding agent with the powder blend. Following granulation, the particles are removed from the granulator and placed in a fluid bed dryer, a vacuum dryer, a microwave dryer, or a tray dryer for drying. Drying conditions are sufficient to remove unwanted granulating solvent, typically water, or to reduce the amount of granulating solvent to an acceptable level. Drying conditions in a fluid bed dryer or tray dryer are typically about 50 to 70° C. The granulate is dried, screened, mixed with additional excipient such as disintegrating agents, flow agents, or compression aids and lubricants such as talc, stearic acid, or magnesium stearate, and compressed into tablets.

In certain embodiments, the tablet may be coated with an optional film-forming agent. This applied film may aid in identification, mask an unpleasant taste, allow desired colors and surface appearance, provide enhanced elegance, aid in swallowing, etc. The amount of film-forming agent may be in the range of about 2% tablet weight to about 4% tablet weight. Suitable film-forming agents are known to one skilled in the art and include hydroxypropyl cellulose, cellulose ester, cellulose ether, one or more acrylic polymer(s), hydroxypropyl methylcellulose, canonic methacrylate copolymers (diethylaminoethyl) methacrylate/methyl-butyl-methacrylate copolymers such as Eudragit E® (Rohm Pharma) and the like. The film-forming agents may optionally contain colorants, plasticizers, fillers, etc. including, but not limited to, propylene glycol, sorbitan monooleate, sorbic acid, titanium dioxide, and one or more pharmaceutically acceptable dye(s).

In certain embodiments, tranexamic acid tablets are formulated by dry blending, rotary compacting, or wet granulating powders composed of tranexamic acid and tablet excipients. These powders are compressed into a tablet.

Alternatively, the tranexamic acid formulations may be administered by pellets or granules in e.g., a sachet or capsule. Tranexamic acid pellets or granules may be prepared by using the pharmaceutically acceptable excipient to form a granule or pellet matrix. U.S. Pat. Nos. 5,650,174, and 5,229,135 each of which is expressly incorporated by reference herein in its entirety, discloses variations on fabricating a pellet or nonpareil dosage form. Spheres are filled into packets, termed sachets, or capsules which are filled by weight to contain the prescribed dose of drug.

In certain embodiments, the tranexamic acid formulations of the present invention may be used for additional indications other than menorrhagia, such as conization of the cervix, epistaxis, hyphema, hereditary angioneurotic edema, a patient with a blood coagulation disorder undergoing dental surgery, combinations thereof, and the like.

Alternatively the tranexamic acid formulations of the invention may be administered as pellets or granules in for example a sachet or capsule.

Additional tranexamic acid formulations are disclosed in U.S. patent application Ser. Nos. 12/228,489, filed Aug. 13, 2008, and 11/346,710, filed Feb. 3, 2006, the disclosures of which are hereby incorporated by reference in their entirety.

Menorrhagia Instrument

With regard to the treatment of menorrhagia (Heavy Menstrual Bleeding) studies of the safety and efficacy of the antifibrinolytic tranexamic acid were conducted. As part of these studies a diagnosis and treatment instrument (Menorrhagia Instrument; MI) was designed. The instrument reliably identifies and monitors heavy menstrual bleeding patients and can be used in conjunction with an antifibrinolytic agent to diagnose and monitor the treatment of heavy menstrual bleeding.

A Menorrhagia Instrument (MI) of the invention reliably captures the diagnosis and treatment of the disease by measuring the impact of treatment on the symptoms associated with heavy menstrual bleeding. The information obtained from individual patient responses to the measures described in the methods of the present invention correlates to blood loss as measured by the alkaline hematin test. For example, data from the measures of social, leisure and/or physical activity symptoms, correlate with the volume of blood loss, and the change in the intensity of these symptoms correlates with the change in volume of blood lost, thus providing a measurement for the successful diagnosis and evaluation of treatment of bleeding disorders.

The instrument of the present invention measures specific aspects of the patient's monthly menstrual period. The measures correlate with the diagnosis of heavy menstrual bleeding and with the course of antifibrinolytic treatment. Further each of the measures individually correlate with quantity of blood loss as measured by the alkaline Hematin test. The symptomatic measures include: 1) a functional assessment measure; and ii) a pharmacology (or therapy assessment) measure.

The functional assessment measure of symptoms is further factored into segments which include 1) a measure of functional impairment generally; 2) impairment of necessary activities; and 3) impairment of discretionary activities.

The pharmacology domain provides an assessment of the severity of the menstrual period.

Specific symptomatic measures may be directed to an initial patient assessment and to the treatment period (pharmacology measure). Examples of specific measures would include examples of initial patient assessment measures (measures 1-4 listed in the Menorrhagia Instrument of FIG. 4); and therapy assessment measures (measures 1-4 together with measures 6, 6a, 6b and 6c contained in the Menorrhagia Instrument of FIG. 4).

In certain embodiments, the present invention is directed to a method of diagnosing and treating heavy menstrual bleeding, wherein the initial diagnoses of heavy menstrual bleeding is accomplished by evaluation of the most recent menstrual period on the basis of one, some or all of the prescribed symptomatic measures of FIG. 4. Measures which may be used as part of the initial patient assessment include, for example: a) determining a patient's perceived blood loss during their most recent menstrual period; b) determining how much the patient's blood loss limited their work outside and inside the home; c) determining how much the patient's blood loss limited their physical activities; d) determining how much the patient's blood loss limited their social and leisure activities; and e) determining the specific activities that were limited by the patient's blood loss.

The assessment of the patient's perceived blood loss during their most recent menstrual period may include an inquiry such as "during your most recent menstrual period, your blood loss was". The assessment may then quantify the patient response as a blood toss that was: i) light, ii) moderate, iii) heavy, or iv) very heavy. Alternatively, the measure may be quantified in terms of a scale of from one to four where one represents light, two represents moderate, three represents heavy and four represents very heavy.

The assessment of a patient's limitation due to the blood loss may include and evaluation of the patient's blood loss limitation on physical activities and/or how much the patient's blood loss limited their social and leisure activities. Assessment of the limitations on work; physical, social and leisure activities may be quantitated as: i) not at all, ii) slightly, iii) moderately, iv) quite a bit, or v) extremely. Alternatively the measure may be quantified in terms of a scale of from one to five where one represents not at all, two represents slightly, three represents moderately, four represents quite a bit, and five represents extremely.

Activities limited may include, but are not limited to, walking, standing, climbing stairs, squatting or bending down, playing with children and attending school activities. Home management activities include, but are not limited to, cooking, cleaning, yard work, and laundry. Leisure activities may include, bin are not limited to, dancing, dinner, and movies. Sports activities may include, but are not limited to, tennis, golf, running, swimming, hiking, biking, boating, baseball, Softball, basketball, soccer, fencing, volleyball, and other sports related activities.

Once the initial patient assessment measures have been completed and the patient has been identified as in need of treatment, the patient is administered a therapeutically effective treatment regimen of an antifibrinolytic agent. Suitable antifibrinolytic agents contemplated for use in the present invention include, but are not limited to tranexamic acid, aminocaproic acid, pharmaceutically acceptable salts, esters, derivatives, pro-drugs, metabolites, and analogues of any of the foregoing antifibrinolytic agents.

In certain embodiments the preferred antifibrinolytic agent is tranexamic acid. The tranexamic acid utilized in the present invention can be formulated into any suitable dosage form. Preferably, the tranexamic acid is in the form of an immediate release tranexamic acid formulation which release is characterized by providing in vitro no more than 95% by weight of the tranexamic acid or a pharmaceutically acceptable salt thereof in about 15 minutes when measured according to USP 27.

When the preferred antifibrinolytic is tranexamic acid, the therapeutically effective treatment regimen contemplated by the present invention includes administration of a single dose of a tranexamic add ranging from about 650 mg to about 1300 mg three (3) times a day for at least one day of menstruation, but not more than five days (or 15 single doses). The treatment regimen may be administered for at least one day; for at least the first two days, for at least the first three days, for days two through three, for days two to three, for the duration of menstruation.

In certain embodiments the tranexamic acid treatment regimen for treating the heavy menstrual bleeding includes administration of a single dose of about 650 mg to about 1.3 gm of a immediate release formulation of the invention three (3) times a day, wherein the immediate release formulation provides, in vitro, no more than 95% by weight of the tranexamic add or a pharmaceutically acceptable salt thereof in about 15 minutes when measured according to USP 27.

In certain other embodiments, the present invention is directed to a method of evaluating the effectiveness of a treatment regimen administered for heavy menstrual bleeding and the amelioration of symptoms associated with heavy menstrual bleeding including limitations on social, leisure, and physical activities.

Evaluation of the effectiveness of the treatment regimen can be initiated at the end of the patient's menstrual period, but prior to completion of the menstrual cycle. The postmenstruation measures provide in part the pharmacology (or therapy assessment) measure described above.

The pharmacology assessment may begin with one or more of the same series of measures utilized during the initial patient assessment, which include: a) determining a patient's perceived blood loss volume during their most recent menstrual period; b) determining how much the patient's blood loss limited their work outside and inside the home; c) determining how much the patient's blood loss limited their physical activities; d) determining how much the patient's blood loss limited their social and leisure activities; e) determining the specific activities that were limited by the patient's blood loss.

Alternatively, an evaluation of the effectiveness of the treatment regimen may require determining the change in the patient's perceived blood loss during the most recent menstrual period in comparison to the blood loss during the patient's previous menstrual period, measure 1 of FIG. 4 and/or an assessment of the improvement achieved, measure 6 of FIG. 4.

For example, a change in the patients perceived blood loss of about one unit for example from "heavy" to "moderate" or from a score of 3 ("heavy") to a score of 2 ("moderate") would provide the basis for continued treatment. While a perceived loss of less man about one unit would suggest either a discontinuation of treatment or a second course after which the evaluation would be reconsidered. Alternatively, or in addition to the blood loss assessment, the practitioner may rely on the assessment in which the comparison of perceived loss is assessed as: i) "about the same", ii) "better", and iii) "worse", as prescribed in measure 6 in FIG. 4. When a patient's response is "about the same", an alternative treatment regimen may be considered for the next menstrual period. The practitioner may also reconsider re-administering the same treatment regimen for an additional menstrual period and later re-evaluate. When a patient's response is "better", the assessment may continue by requiring the patient to provide further information about the improvement in menstrual bleeding. For example, the assessment may include "if your menstrual bleeding improved since your last period, please indicate how much" (measure 6b of the MI of FIG. 4). Answers to this inquiry about an improvement in menstrual bleeding may require the patient to provide an answer such as: i) a very great deal better, ii) a great deal better, iii) a good deal better; iv) an average amount better; v) somewhat better, vi) a little better; or vii) almost the same, hardly better at all.

Alternatively the answers can be scaled on a seven unit scale where "a very great deal better" is assigned a value of 7 and "almost the same" is valued as 7.

When a patient's response to measure 6 is "worse", the inquiry continues by requiring the patient to provide further data characterizing the change in menstrual bleeding. For example, the inquiry may determine "if your menstrual period worsened since your last period, please indicate how much" (measure 6c of MI of FIG. 4). Data for this measure to a worsening in menstrual bleeding may require the patient to provide a ranking such as: i) "a very great deal worse"; ii) "a great deal worse"; iii) "a good deal worse"; iv) "an average amount worse"; v) "somewhat worse"; vi) "a little worse"; or vii) "almost the same, hardly worse at all". As before the answers may be scaled on a seven unit scale where −1 is "almost the same" and −7 is "a very great deal worse".

Figure 5:
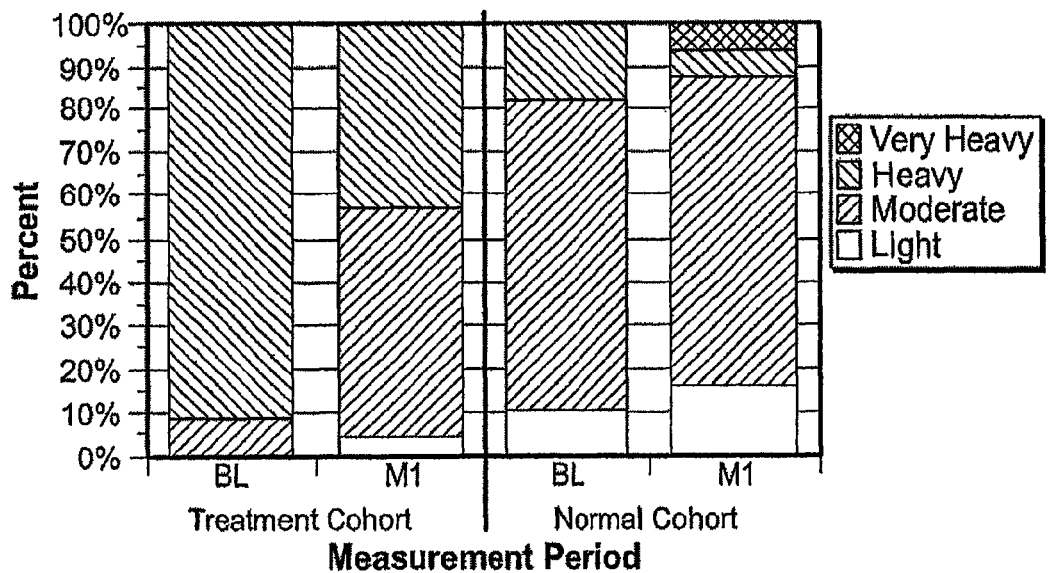
FIG. 5 is a graph of Menorrhagia Instrument measure #1 percentage of patients and normals indicating each response at baseline (BL) and at one (1) month (M1) from Example 5.
Figure 6:
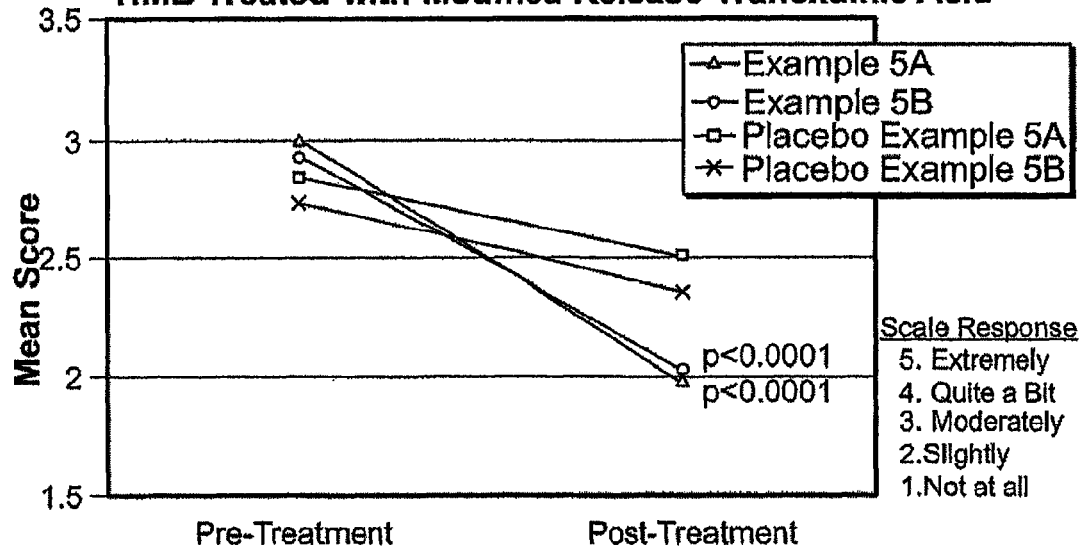
FIG. 6 is a graph of the limitations of social and leisure activities (LSLA) in women with Heavy Menstrual Bleeding (HMB) in accordance with the treatment regimens administered in Examples 5A and 5B.
Figure 7:
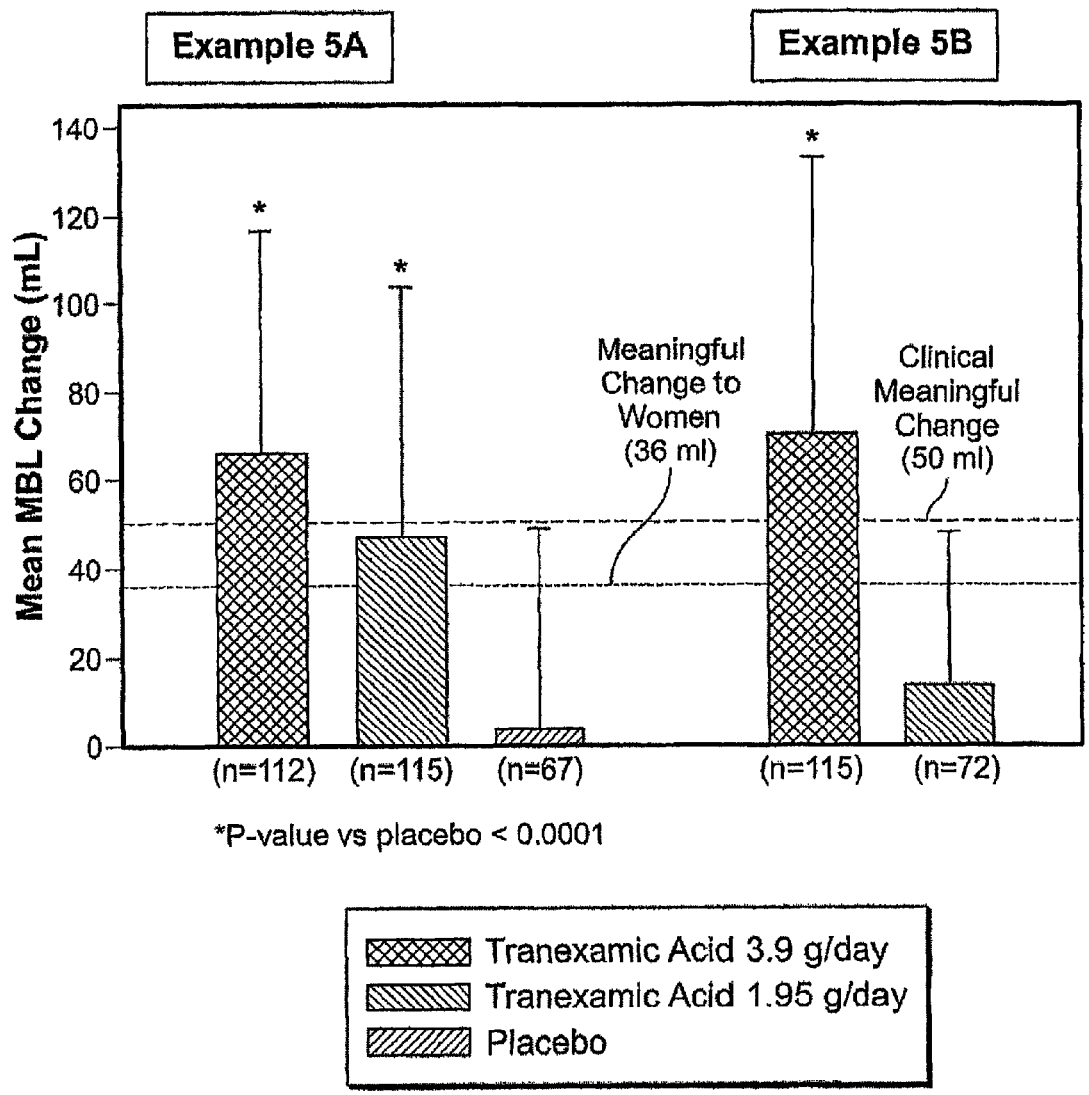
FIG. 7 is a graph of the mean menstrual blood loss change from the clinical studies of Example 5A and 5B.

The comparison of perceived blood loss which results in an improvement of at least about one unit as measured by measure 1 of FIG. 5 and/or an assessment of a perceived blood loss which is "better" as provided in measure six of FIG. 1 may proceed by assessing whether the improvement "was meaningful or an important change" to the patient (measure 6c of MI of FIG. 4).

The information obtained about the "improvement" or "worsening" in menstrual bleeding allows the practitioner to make an evaluation of the effectiveness of the treatment regimen which correlates with the change in blood loss as measured by the alkaline hematin test and demonstrated with clinical trial data.

The method for evaluating the effectiveness of a treatment regimen of the present invention may be repeated after each menstrual period. The data obtained from the initial patient assessment and the subsequent pharmacology (therapy assessment) can be stored into a computer database and utilized for future diagnostic and/or evaluation purposes.

In certain other embodiments, the present invention is directed to a method of treating heavy menstrual bleeding. The method involving, evaluating symptomatic data gathered from the measures individually or collectively as described in FIG. 4 (items one through four and six as discussed above) to determine the need for therapy and then administering, to a patient in need, a therapeutically effective treatment regimen of an antifibrinolytic agent, e.g. a release modified tranexamic acid formulation or a bioequivalent immediate release formulation of the invention, wherein the treatment regimen is to be administered for part or for the duration of menstruation, but no longer than 5 days during the patient's menstrual cycle.

The present invention is further described with regard to the following examples.

DETAILED DESCRIPTION OF PREFERRED EMBODIMENTS

The invention will be further appreciated with respect to the following non-limiting examples. Other variations or embodiments of the invention will also be apparent to one of ordinary skill in the art from the above descriptions and examples. Thus, the forgoing embodiments are not to be construed as limiting the scope of this invention.

Example 1

In Example 1, immediate release 650 mg tranexamic acid tablets were prepared having the ingredients listed in Table 1 below:

TABLE 1

| Ingredient | Quantity per batch (kg) | Quantity per tablet (mg) |
|---|---|---|
| Active Ingredient | | |
| Tranexamic Acid, EP (650 mg/tab) | 84.50 | 650.0 |
| Inactive Ingredients | | |
| Microcrystalline Cellulose, NF (Avicel PH 101) | 5.753 | 44.25 |
| Microcrystalline Cellulose, NF (Avicel PH 102) | 10.660 | 82.00 |
| Colloidal Silicon Dioxide, NF | 0.0975 | 0.75 |
| Pregelatinized Corn Starch, NF | 6.435 | 49.50 |
| Croscarmellose Sodium, NF | 19.50 | 15.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water, USP* | 17.550 | 135.00 |
| Film Coating (Inactive Ingredients)** | | |
| Opadry White YS-1-7003 | 4.110 | — |
| Purified Water, USP | 36.990 | — |

*Purified water is removed during processing
**6 kg excess prepared to account for losses during transfer The formulation of Example 1 was prepared as follows:

1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulate equipped with a #30 mesh screen. Weigh the granulation. Add granulation to the V-Blender.
9. Add the croscarmellose sodium and MCC to the V-Blender and blend.
10. Pass magnesium stearate and stearic acid through oscillating granulate equipped with a #40 mesh screen. Add magnesium stearate and stearic acid to the V-blender and blend.
11. Perform specified physical property testing. Proceed to compression.
12. Compress tablets.
12. After compression, spray coat the compressed dosage forms with the Opadry White in water.

Example 2

Modified release 650 mg tranexamic acid tablets were prepared having the ingredients listed in the Table 2 below:

TABLE 2

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |

*Purified water is removed during processing

The formulation of Example 2 was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.
7. Dry the granulation to moisture content of NMT 1.2%.
8. Pass the granulation through the oscillating granulator equipped with a #30 mesh screen. Weigh the granulation. Add granulation to the V-Blender.
9. Add the hypromellose USP Methocel K3 Premium to the V-blender. Blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets to desired weight.

Example 3

In Example 3, modified release 650 mg tranexamic acid tablets were prepared as in Example 1 and coated with a film coating similar to the immediate release tablets of Example 2. The ingredients are listed in Table 3 below.

TABLE 3

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Colloidal Silicon Dioxide NF | 0.0975 | 0.75 |
| Pregelatinized Corn Starch, NF | 6.435 | 49.50 |
| Hypromellose, USP (Methocel K3 Premium LV) | 19.110 | 147.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |
| Film Coating (Inactive Ingredients)** | | |
| Opadry White YS-1-7003 | 4.305 | — |
| Purified Water, USP | 38.750 | — |

*Purified water is removed during processing
**6 kg excess prepared to account for losses during transfer

Example 3A

Example 3A, delayed release 650 mg tranexamic acid tablets were prepared having the ingredients listed in Table 3A below:

TABLE 3A

| Ingredient | Quantity per batch (kg) | Quantity per tablet (mg) |
|---|---|---|
| Active Ingredient | | |
| Tranexamic Acid, EP | 84.50 | 650.0 |
| Inactive Ingredients | | |
| Microcrystalline Cellulose NF (Avicel PH 101) | 5.753 | 44.25 |
| Microcrystalline Cellulose NF (Avicel PH 102) | 10.660 | 82.00 |
| Colloidal Silicon Dioxide NF | 0.0975 | 0.75 |
| Pregelatinized Corn Starch, NF | 6.435 | 49.50 |
| Croscarmellose Sodium NF | 19.50 | 15.00 |
| Povidone, USP (K value range 29-32) | 4.680 | 36.00 |
| Stearic Acid, NF (powder) | 2.340 | 18.00 |
| Magnesium Stearate, NF (powder) | 0.585 | 4.50 |
| Purified Water USP* | 17.550 | 135.00 |
| Film Coating (Inactive Ingredients)** | | |
| Acryl-Eze (930185359) | 12.90 | — |
| Silicone Emulsion, 30% | 0.323 | — |
| Purified Water, USP | 51.271 | — |

*Purified water is removed during processing; mg per tablet is based on theoretical specific gravity of 1.0 g/ml
**6 kg excess prepared to account for losses during transfer The formulation of Example 3A was prepared as follows:
1. Weigh all ingredients and keep in moisture resistant containers until ready for use.
2. Measure water into a container. Mix povidone at medium speed until completely dissolved.
3. Add tranexamic acid, microcrystalline cellulose (MCC), pregelatinized corn starch, and colloidal silicon dioxide to the high shear mixer.
4. Mix using impeller only.
5. Mix for an additional time (impeller only). Add all of the povidone solution during this mixing step.
6. Mix until adequately granulated (impeller and chopper). Proceed only when desired granulation has been achieved. Add additional water if necessary.

7. Dry the granulation to moisture content of NMT 1.2%.
8. Pass the granulation through the oscillating granulator equipped with a #30 mesh screen. Weigh the granulation. Add granulation to the V-Blender.
9. Add the croscarmellose sodium and MCC to the V-Blender and blend.
10. Pass magnesium stearate and stearic acid through oscillating granulator equipped with a #40 mesh screen. Add magnesium stearate and stearic acid to the V-blender and blend.
11. Perform specified physical property testing. Proceed to compression.
12. Compress tablets.
13. After compression, spray coat the compressed dosage forms with the firm coating.

Dissolution results for the delayed release formulation of Example 3A (in base stage) are listed below in Table 3B.

Dissolution Results for the Delayed Release Formulation

In Base Stage

TABLE 3B

| Time (min.) | Dissolution (%) | Standard Deviation |
|---|---|---|
| 15 | 16% | ±6.013873 |
| 30 | 89% | ±14.06769 |
| 45 | 95% | ±2.810694 |
| 60 | 97% | ±2.345208 |

Example 4

Bioavailability and Bio Equivalence Evaluation

In Example 4, a comparative, randomized, single dose, 4-way Crossover Absolute Bioavailability (BA) and Bioequivalence (BE) study of Tranexamic Acid Tablet Formulations prepared in accordance with Examples 1 and 2 in Healthy Adult Women Volunteers under Fasting Conditions was performed. The objective was to assess the bioequivalence of a 650 mg immediate release tablet formulation prepared in accordance with Example 1 compared to the modified release tablet formulation of tranexamic acid prepared in accordance with Example 2, and to determine the bioavailability of the tablet formulations to the approved IV (1 g) formulation Cyklokapron® by Pharmacia & Upjohn. The design was a randomized, 4-way crossover, comparative BE and BA determination. All oral doses administered were 1.3 g. Twenty-eight (28) healthy non-smoking adult female volunteer subjects were enrolled in the study. Sample size was calculated assuming a 25% CV in $AUC_{inf}$. The study endpoints were the 90% confidence intervals of the ratio of least-squares means of the pharmacokinetic parameters $AUC_{0-t}$, $AUC_{inf}$ and $C_{max}$ of the modified release formulation to the immediate-release formulation from serum concentration-time data drawn up to 36 hours after a single dose of drug. In addition, the bioavailability of the tablet formulations were calculated. Smokers, oral contraceptive users, those with a previous history of thromboembolic events and altered vision were excluded from the study. ECG monitoring was performed before, during and after the estimated times of peak serum tranexamic acid concentrations exposure. Adverse events were captured and recorded throughout the trial period.

In the study, subjects were randomized to receive single oral 1.3 g (2×650 mg tablets) dose of tranexamic acid in tablet forms which included a modified release dosage form and an immediate release dosage form. Subjects were also administered a single 1 g (10 ml) IV solution of tranexamic acid (100 mg/ml concentration).

A summary of the pharmacokinetic results from the study of Example 4 are listed in the tables below.

TABLE 4

Summary of Results - Tranexamic Acid in Plasma Pharmacokinetic Parameters (N = 26)

| | ln AUC 0-t* (mcg · h/mL) | ln AUCinf* (mcg · h/mL) | ln Cmax* (mcg/mL) |
|---|---|---|---|
| Modified Release formulation | | | |
| Mean | 66.703 | 69.642 | 11.251088 |
| CV | 26.8 | 27.2 | 29.1 |
| N | 26 | 24 | 26 |
| Immediate Release formulation | | | |
| Mean | 70.157 | 72.656 | 12.260414 |
| CV | 16.2 | 16.4 | 23.0 |
| N | 26 | 24 | 26 |
| Least-Squares Mean: | | | |
| Modified Release | 66.935 | 68.891 | 11.321919 |
| Immediate Release | 70.051 | 72.411 | 12.258222 |
| Ratio of Least-Squares Mean (modified release/immediate release) % | 95.6 | 95.1 | 92.4 |

*For ln-transformed parameters, the antilog of the mean (i.e. the geometric mean) is reported.
AUCinf, kel, half-life and F could not be estimated for some subjects.

TABLE 5

Summary of Results - Tranexamic Acid in Plasma Pharmacokinetic Parameters (N = 26)

| | Tmax (h) | Half-life (h) | kel (1/h) | F (%) |
|---|---|---|---|---|
| Modified Release formulation | | | | |
| Mean | 2.942 | 11.370 | 0.06300 | 44.93 |
| CV | 22.7 | 17.6 | 19.4 | 25.3 |
| n | 26 | 26 | 26 | 24 |
| Immediate Release formulation | | | | |
| Mean | 2.808 | 11.013 | 0.06438 | 46.04 |
| CV | 20.8 | 15.5 | 15.3 | 16.1 |
| n | 26 | 24 | 24 | 24 |

TABLE 6

Summary of Results - Tranexamic Acid in Plasma
Pharmacokinetic Parameters
(N = 26)

|  | Ln AUC 0-t*<br>(mcg · h/mL) | ln AUCinf*<br>(mcg · h/mL) | ln Cmax*<br>(mcg/mL) |
|---|---|---|---|
| 90% Confidence<br>Intervals<br>(Modified<br>release/Immediate<br>release) % |  |  |  |
| lower limit: | 87.8% | 87.4% | 84.0% |
| upper limit: | 104.0% | 103.5% | 101.6% |
| p-Value (ANOVA) |  |  |  |
| Modified vs Immediate | 0.3721 | 0.3259 | 0.1676 |
| Period | 0.0704 | 0.0499 | 0.0356 |
| Sequence | 0.7734 | 0.7978 | 0.8207 |
| Intrasubject CV % | 18.3 | 17.4 | 20.6 |

*For ln-transformed parameters, the antilog of the mean (i.e, the geometric mean) is reported.
AUCinf, kel, half-life and F could not be estimated for some subjects.
AUC 0-t is the area under the plasma concentration versus time curve, from time 0 to the last measurable concentration, as calculated by the linear trapezoidal method.

Figure 2:
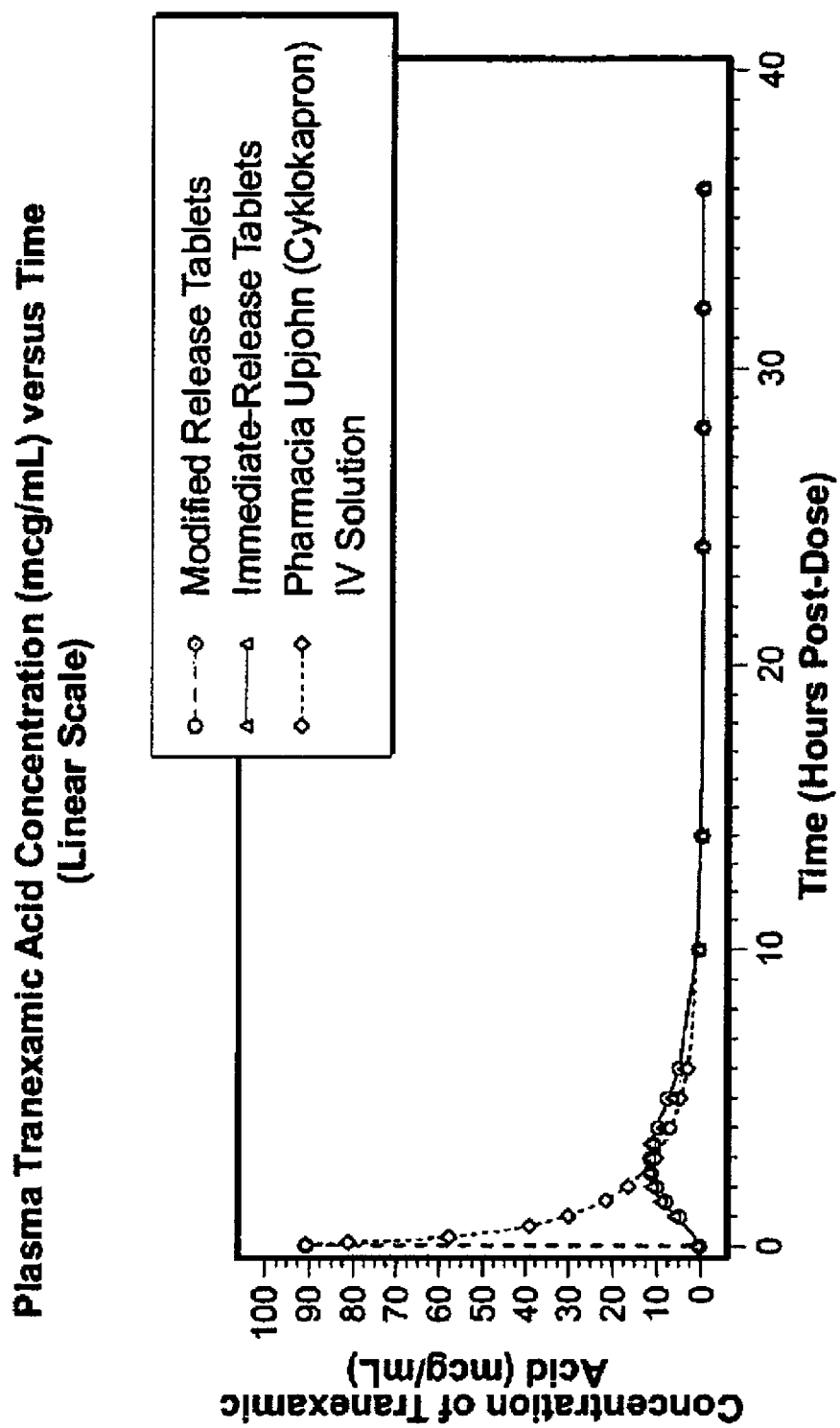
FIG. 2 depicts mean plasma concentration-time profiles on a linear scale over 36 hours for the formulations of Examples 1 and 2 compared to IV tranexamic acid (Cyklokapron).
Figure 3:
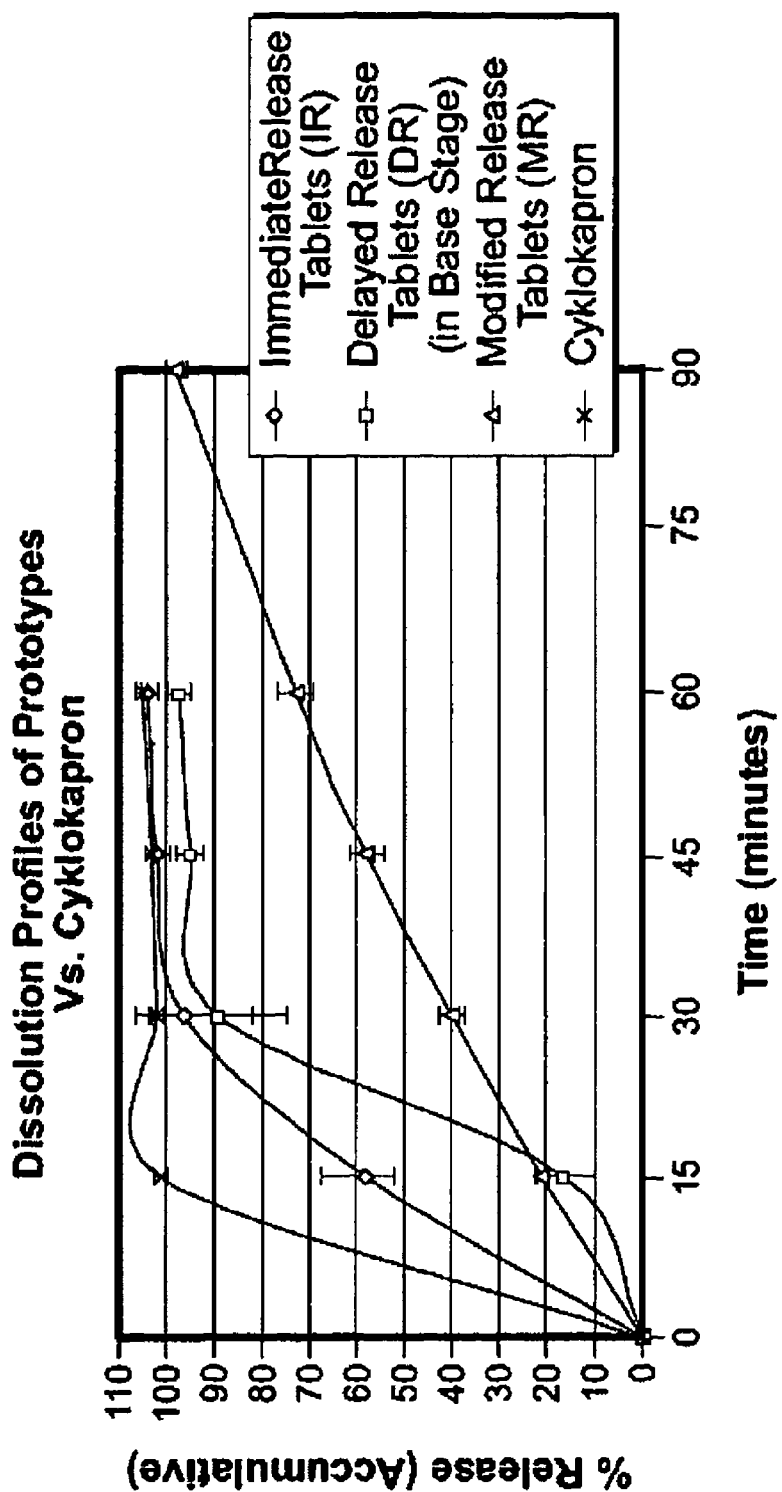
FIG. 3 depicts the dissolution profiles of the modified release tranexamic acid formulation of Example 2; the immediate release tranexamic acid formulation of Example 1; the delayed release tranexamic acid formulation of Example 3A, and the commercial Cyklokapron immediate release formulation of Example 4A.

Concentration-time profiles for the study of Example 4 are presented on semi-log and linear scale over 36 hours and are depicted in FIGS. 1 and 2.

The following pharmacokinetic parameters in the table below were calculated for tranexamic acid in plasma for the study of Example 4.

MRT: The mean residence time (MRT) after intravenous administration of tranexamic acid was determined using the equation, AUMC/AUC+infusion time/2.

where the AUMC is the area under the moment-time curve.

MTT: Following oral administration of the Modified Release and Immediate Release formulations, the mean transit time (MTT) of tranexamic acid was calculated by dividing the AUMC by the AUC.

MAT: The mean absorption time (MAT) for the two formulations was derived by subtracting the MRT from the MTT.

Mean (±SD) results are presented in the table below:

TABLE 7

|  | IV | Modified Release | Immediate Release |
|---|---|---|---|
| MRT (hours) | 3.51 ± 0.38 | N/A | N/A |
| MTT (hours) | N/A | 7.70 ± 0.72 | 7.21 ± 1.01 |
| MAT (hours) | N/A | 4.18 ± 0.70 | 3.70 ± 0.94 |

The mean transit time (MTT) and mean absorption time (MAT) of the Modified Release formulation of tranexamic acid was approximately 30 minutes longer than that observed for the Immediate Release formulation.

The most frequently reported adverse events from the study of Example 4 are listed in the table below. The table lists the number of subjects reporting adverse events, and the percentage of subjects is in parentheses.

TABLE 8

|  | Treatment | | |
|---|---|---|---|
| Adverse Events | Modified<br>Release<br>(2 × 650 mg)<br>(n = 27) | Immediate<br>Release<br>(2 × 650 mg)<br>(n = 27) | IV solution<br>(10 ×<br>100 mg/ml)<br>(n = 27) |
| Headache | 4 (15%) | 7 (26%) | 7 (26%) |
| Nausea | 0 (0%) | 2 (7%) | 10 (37%) |
| Dizziness | 0 (0%) | 0 (0%) | 11 (41%) |
| Feeling Hot | 0 (0%) | 0 (0%) | 6 (22%) |
| Nasal Congestion | 2 (7%) | 1 (4%) | 1 (4%) |
| Cough | 0 (0%) | 0 (0%) | 2 (7%) |
| Urine odor abnormal | 2 (7%) | 0 (0%) | 1 (4%) |

Dissolution Results for Immediate Release and Modified Release Formulations prepared in accordance with Examples 1 and 2 respectively used in the study of Example 3 tested under USP 27 Apparatus Type II Paddle Method @ 50 RPM in 900 ml water at 37±0.5° C. are listed in the tables below.

TABLE 9

Dissolution Results for the Immediate Release Formulation in Table 1.

| Time (min.) | Dissolution (%) | Standard Deviation |
|---|---|---|
| 15 | 58.0% | ±9.521905 |
| 30 | 96.0% | ±10.2697 |
| 45 | 102.0% | ±0.408248 |
| 60 | 104.0% | ±1.032796 |

TABLE 10

Dissolution Results for the Modified Release Formulation in Table 2

| Time (min.) | Dissolution (%) | Standard Deviation |
|---|---|---|
| 15 | 21.0% | ±1.414214 |
| 30 | 40.0% | ±2.810694 |
| 45 | 58.0% | ±3.600926 |
| 60 | 73.0% | ±3.81663 |
| 90 | 98.0% | ±2.097618 |

Conclusions:

The ratios of least-squares means and the 90% confidence intervals derived from the analyses of the ln-transformed pharmacokinetic parameters $AUC_{0-t}$, $AUC_{inf}$ and $C_{max}$ for tranexamic acid in plasma were within the 80-125% Food and Drug Administration (FDA) acceptance range for the modified release formulation versus the immediate release formulation under fasting conditions.

The absolute bioavailability of the modified release and immediate release tablet formulations were 44.93% and 46.04% respectively Based on these results, the modified release tranexamic acid tablet formulation and the immediate release tranexamic acid formulation are bioequivalent under fasting, conditions.

Example 4A

Comparative Example

In Comparative Example 4A, a 500 mg immediate release tranexamic acid tablet, approved and marketed in Canada under the name Cyklokapron was obtained and dissolution tested under USP 27 Apparatus Type II Paddle Method @ 50 RPM in 900 ml water at 37±0.5° C. The dissolution results are listed in Table 11 below:

TABLE 11

| Sample # | % dissolved in 15 min. | % dissolved in 30 min. | % dissolve in 45 min. | % dissolved in 60 min. |
|---|---|---|---|---|
| 1 | 102 | 104 | 105 | 106 |
| 2 | 102 | 104 | 105 | 106 |
| 3 | 101 | 102 | 102 | 105 |
| 4 | 99 | 101 | 102 | 103 |
| 5 | 100 | 102 | 103 | 104 |
| 6 | 99 | 101 | 102 | 104 |
| Average | 101 | 102 | 103 | 105 |
| % RSD | 1.4 | 1.3 | 1.4 | 1.1 |

Example 5

Menorraghia Impact Measure Validation

Objective measurements of menstrual blood loss are not practical in the healthcare setting, and they correlate poorly with a woman's subjective assessment of blood loss and its impact on quality of life [Warner 2004; National Collaborating Centre for Women's and Children's Health, 2007]. Menorrhagia is a subjective condition and may be practically defined as menstrual loss that is greater than the woman feels that she can reasonably manage. The amelioration of symptoms of heavy menstrual loss are practical efficacy benefits of the treatment are therefore important to measure and validate in a controlled clinical environment.

The MI was evaluated in a sub population of patients enrolled in a clinical trial designed to assess the safety and efficacy of modified release tranexamic acid formulation (Example 2) at an oral dose of 3.9 g administered daily for up to 5 days during each menstrual period (While the present study was conducted utilizing the modified release tranexamic acid formulation described herein in Example 2, the effectiveness of the MI can also be evaluated utilizing the immediate release and delayed release formulations described herein). Two groups of patients were used to assess the MI, one group of patients were those diagnosed with menorrhagia and undergoing treatment. The second group was an age matched normal group. The sub-study was designed to collect sufficient quantitative data to support the construct-related validation of the MI measures; to collect sufficient quantitative data to support the assessment of meaningful/important change in blood loss to the women; to conduct a test/retest evaluation of the instrument, and to address the reliability of the MI measures.

Study Methods

Development of the MI began with a review of the literature focusing on the methods used to collect qualitative data from menorrhagia patients. Qualitative interviews with patients determined which symptomatic concepts were most important to women and could be included in a draft Impact Measure. Cognitive debriefing interviews to evaluate patient understanding of items led to the synthesis of a patient-based instrument for assessing the impact of limitations caused by heavy menstrual bleeding. Published measures were used in the evaluation of the psychometric properties of the Menorrhagia Instrument to assess Construct-Related Validity. The reference measures include, the Ruta Menorrhagia Questionnaire [Ruta 1995] and the Medical Outcomes Study Short-Form 36 Item Health Status Instrument (SF-36) [Ware 1992]. Scoring of the standardized measures followed published algorithms, Table 12.

TABLE 12

Descriptions of Instruments used in this study

| Measure | Score Generated | Score Ranges |
|---|---|---|
| Menorrhagia Impact Measure (MI) | Blood Loss Severity (Q1) | 1 (light) thru 4 (very heavy) |
| | Limitation | |
| | Work outside or inside the home (Q2) | 1 (not at all) thru 5 (extremely) |
| | Physical activities (Q3) | 1 (not at all) thru 5 (extremely) |
| | Social or leisure activities (Q4) | 1 (not at all) thru 5 (extremely) |
| | Activity list (Q5) | [Descriptive] |
| | Change in blood loss (follow-up) (Q6, 6a, 6b) | [15-pt scale: 0 = no change, 1-7 improve, 1-7 worse] |
| | Meaningful/important change (Q6c) | Y/N |
| Ruta Menorrhagia Questionnaire | Global | 0 (asymptomatic) - 42 (severe) |
| | Specific | |
| | Physical Function: Impact on work and daily activities (Q9 and Q10) | 0 (asymptomatic) - 6 (severe) |
| | Social Function: Impact on social and leisure activities and sex-life (Q11 and Q12) | 0 (asymptomatic) - 8 (severe) |
| SF-36 | Physical Functioning, Role-Physical, Bodily Pain General Health (can be combined to form Physical Health Component Score); Vitality, Social Functioning, Role-Emotional, Mental Health (can be combined to form Mental Health Component Score) | 0-100 (100 = minimal impairment) |

Study Design

A total of 262 women completed the MI. The MI measures 1 through 5 were administered after subject's baseline period and after the subsequent first, second, third and sixth treatment periods. The MI measure 6 was administered after the first treatment period only. For this validation study, only the data collected through Month 1 of treatment was included in the analyses for the treatment cohort. The MI measures 1-5 were administered at baseline add at die subsequent first and second non-treatment periods for the subjects in the normal cohort The MI measure 6 was administered and data collected, at Month 1 and Month 2. The Ruta Menorrhagia Questionnaire, SF-36 Health Survey and the MI were completed by the subject before visit procedures were performed. A subset of at least 50 subjects were asked to return to the study site 7 to 10 days after the baseline Visit but before the next menstrual period starts to complete the MI a second time.

Treatment Group

A total of 177 patients were enrolled into the sub-study. During this time period 28 patients withdrew consent dropped-out or did not properly complete MI and were non-evaluable. The 149 patients remaining were intended to be age matched. The majority of patients in the study were in their late 30's or early 40's. Because of the difficulty of enrolling sufficient numbers of women with normal menstrual periods in this age bracket 18 evaluable patients were not age matched. A total of 131 evaluable patients were age matched. A sub-set of 80 evaluable patients participated in the test/retest segment of the validation. Of these patients 11 were evaluable but not age matched. Data from all 80 patients were used for statistical evaluation of the test/re-test correlations.

Normal Group

A group of women with self reported normal menstrual bleeding comprised the pool of normal women eligible for age matching in the study. A normal was defined as all of the following: a menstrual cycle between 26 and 32 days long, and their last (most recently completed) menstrual period was seven days or less in duration, the heaviest bleeding was three days or less, and the woman classified the bleeding overall as "light" or "moderate" as opposed to "heavy" or "very heavy." Women with normal periods who were enrolled into the study served as age-match controls for women recruited into the treatment group. Un-matching and re-matching occurred throughout the enrollment period if participants in either group dropped out of the study, if better re-matching increased the total number of matched pairs, or if the age-matched woman with normal periods did not enroll in the study.

Five women enrolled in the study did not/complete the study through Visit 3. Another five women who did complete the study became 'unmatched' as the Treatment Group participant they had been matched to became non-evaluable. The 131 women who completed the study and remained matched are the Validation Sample Normal Group. A total of 51 women completed the Retest.

The following Measures were summarized and statistically analyzed:
MI measure 1—Blood Loss Rating
MI measure 2—Limitation of Work Outside or Inside the Home
MI measure 3—Limitation of Physical Activities
MI measure 4—Limitation of Social or Leisure Activities
MI measure 6/6a/6b—Menstrual Blood Loss During Last Period
MI measure 6c—Meaningfulness of Change in Menstrual Blood Loss The statistics include the counts (missing data), mean, standard deviation, median, inter-quartile range, and minimum/maximum values. Differences in these variables between the treatment and normal cohorts were assessed using analysis of variance.

A p-value <0.05 was required for significance using two-sided hypothesis tests; no p-value adjustments were made for the analysis of multiple endpoints. All analyses were performed under SPSS version 11.5 for Windows, and the Stuart-Maxwell test for homogeneity was performed using Stata version 9.0 for Windows.

Validation of the MI was conducted using standardized analytic procedures found in the FDA Draft Guidance on Patient Reported Outcomes for Use in Evaluating Medical Products for Labeling Claims and instrument review criteria developed by the Scientific Advisory Committee of the Medical Outcomes Trust.[1]

[1] Scientific Advisory Committee of the Medical Outcomes Trust. Assessing health status and quality-of-life instruments: attributes and review criteria. Qual Life Res. 2002; 11: 193-205

Evaluation of the Menorrhagia Instrument

The MI consisted of 4 individual measures (1-4) that were analyzed separately for validation. No summative scale was derived. Measure 5, served as descriptive of variables and did not undergo standard validation analyses. Measures 6, 6a and 6b dealt with menstrual blood loss relative to the previous menstrual period. The answers to the measures in the subparts of measure 6, were combined to produce a 15 point rating scale. The scale values range from −7 to +7 with −7 representing a very great deal worse menstrual blood loss than the previous period, and +7 representing a very great deal better menstrual blood loss than the previous period. The midpoint (0) represents the perception of about the same menstrual blood loss as the previous period.

Test-retest reliability assessed if items produced stable, reliable scores under similar conditions (Guttman, 1945). Reproducibility was evaluated in a subset of at least 50 from the treatment group and at least 50 from the normal group 7 to 10 days after the baseline visit using the intra-class correlation coefficient (ICC, see formula below). Values above 0.70 indicated the stability of an instrument over time. The following formula was used to compute the Intraclass Correlation Coefficient (ICC):

$$ICC = \frac{A^2 + B^2 + C^2}{A^2 + B^2 + D^2 - \left(\frac{C^2}{n}\right)}$$

where:
A=Standard deviation of baseline score
B=Standard deviation of Time 2 score
C=Standard deviation of change in score
D=mean of change in score
n=number of respondents The data for each of the measures was above 0.70. In the test population, n=88, values of 0.72 (0.60-0.81), 0.75 (0.64-0.83), 0.77 (0.67-0.84) and 0.76 (0.66-0.84) for measures 1 to 4 respectively, the aged matched normal values where n=51 were 0.77 (0.63-0.86), 0.67 (0.49-0.80), 0.75 (0.60-0.85) and 0.86 (0.77-0.92) respectively.

Construct-Related Validity was established when relationships among items, domains, and concepts conform to what was predicted by the conceptual framework for the instrument This includes convergent discriminant, and known-groups validity. Convergent and discriminant validity was present where measures of the same construct are more highly related and measures of different constructs were less related. To assess convergent and discriminant validity, Pearson's correlation coefficients were computed between each MI measure and items and scales from the SF-36 and the Ruta Menorrhagia Questionnaire included in the study design and administered at the same visit. The following hypotheses were tested.

The MI Blood Loss Measure (#1) will have a stronger association with the Ruta Menorrhagia Questionnaire (RMQ) than to the SF-36 subscales.

The MI Physical Activity Limitation Measure (#3) will have a stronger association with the RMQ Physical Function scale, the SF-36 Physical domain, the SF-36 Role-Physical domain, and SF-36 Physical Component Summary score than the Ruta Social, SF-36 Social, and SF-36 Vitality domains.

The MI Social/Leisure Activity Limitation will have a have stronger associations with the RMQ Social Function scale and the SF-36 Social Function domain than the RMQ Physical, the SF-36 Physical and SF-36 Bodily Pain domains.

For convergent validity, the correlations of MI measures with Ruta subscales, SF-36 subscales, and diary data are shown in Table 13. The Ruta global score was highly correlated with each MI measures (range 0.757-0.809). The correlations of items with the SF-36 subscales were low to moderate, which is to be expected since the SF-36 is not a disease-specific measure, but rather a more generic health status measure unable to detect differences between a normal population and a population of women with menorrhagia. The MI measures were more strongly correlated with the SF-36 Physical and Role Physical subscales than other SF-36 subscales.

TABLE 13

Correlations Between Menorrhagia Instrument Patient Reported Outcome (PRO) Measures and Ruta/SF-36/Diary

|  | MI measure 1 Blood Loss | MI measure 2 Limit work outside or inside home | MI measure 3 Limit physical activity | MI measure 4 Limit social or leisure activity |
|---|---|---|---|---|
| Ruta - Global | 0.767 (0.000) | 0.785 (0.000) | 0.807 (0.000) | 0.809 (0.000) |
| Ruta - Physical Fx | 0.512 (0.000) | 0.682 (0.000) | 0.646 (0.000) | 0.664 (0.000) |
| Ruta - Social Fx | 0.606 (0.000) | 0.634 (0.000) | 0.659 (0.000) | 0.683 (0.000) |
| SF-36 - Physical Fx | −0.229 (0.000) | −0.234 (0.000) | −0.264 (0.000) | −0.273 (0.000) |
| SF-36 - Social Fx | −0.118 (0.057) | −0.194 (0.002) | −0.200 (0.001) | −0.261 (0.000) |
| SF-36 - Role Physical | −0.200 (0.001) | −0.279 (0.000) | −0.258 (0.000) | −0.303 (0.000) |
| SF-36 - Vitality | −0.143 (0.021) | −0.193 (0.002) | −0.248 (0.000) | −0.250 (0.000) |
| SF-36 - Bodily Pain | −0.087 (0.163) | −0.168 (0.006) | −0.192 (0.002) | −0.205 (0.001) |
| SF-36 - PCS | −0.190 (0.002) | −0.271 (0.000) | −0.285 (0.000) | −0.275 (0.000) |

The data supported the hypothesis that the MI Blood Loss measure (#1) had a stronger association with the Ruta global score than to the SF-36 subscales. While the hypothesis that MI measure #3 (Physical Activity Limitation) would be strongly associated to the physical domains of the RMQ (r=0.65) and SF-36 (r=0.26) was confirmed, this measure was also strongly correlated to the RMQ Social Functioning (r=0.66). MI measure #4 (Social or Leisure Activity Limitation) was highly correlated to the RMQ Social (r=0.68) and moderately associated with the SF-36 Social Functioning domain.

Known-groups validity determined the ability of the instrument to discriminate between groups of subjects known to be distinct. The ability of the MI items to discriminate among known groups was assessed by comparing the 4 items (1 thru 4) to responses from the two groups (treatment and normal) at baseline. Differences in these variables, between the treatment and normal groups, were assessed using analysis of variance. A p-value <0.05 was required for significance using two-sided hypothesis tests; no p-value adjustments was made for the analysis of multiple endpoints.

For each MI measure, the mean score for the treatment group was significantly different than the mean score for the normal group (p<0.001). The treatment group scores were higher for each individual measure, indicating greater limitation as a result of their excessive menstrual blood loss (see Table 14).

TABLE 14

Known-Groups Validity of the MI

|  |  | Treatment Cohort | | | AGE MATCH NORMAL Cohort | | | |
|---|---|---|---|---|---|---|---|---|
|  |  | N | Mean | St. Dev. | N | Mean | St. Dev. | F (sig.)[1] |
| MI measure 1 | Self-perceived blood loss | 131 | 3.25 | 0.61 | 131 | 2.10 | 0.61 | 234.727 (<0.001) |
| MI measure 2 | Limit you in your work | 131 | 3.04 | 0.99 | 131 | 1.34 | 0.59 | 286.844 (<0.001) |
| MI measure 3 | Limit you in your physical activities | 131 | 3.28 | 0.95 | 131 | 1.49 | 0.72 | 299.011 (<0.001) |
| MI measure 4 | Limit you in your social/leisure activities | 131 | 3.05 | 1.06 | 131 | 1.37 | 0.72 | 227.312 (<0.001) |

The ability to detect change required that values for the item or instrument change when the concept it measures changed. In order to measure the MI items ability to detect change, longitudinal data were evaluated focusing primarily on the changes from baseline to month 1. Differences in proportions and comparisons between treatment and normal groups were compared using chi-square statistics (the Stuart-Maxwell test testing marginal homogeneity for all categories simultaneously). Cohen Effect Size statistics were also compared between the treatment and normal groups. The Cohen Effect Size was computed by taking the mean change in measure score (baseline to month 1) and dividing that by the standard deviation of mean baseline score[2].

2 Cohen, J. J. (1988). Statistical power analysis for the behavioral sciences (p. 8). Erlbaum: Hillsdale, N.J.

Ability to detect change was described for each item in Tables 15A-D by indicating the distribution of baseline and month 1 response option pairs for all patients. Change in responses from baseline to mouth 1 was tested using the Stuart-Maxwell test. For the treatment group, there was significant change in responses to each measure from baseline to month one (p<0.001). For the normal group, none of the items had significant changes in responses from baseline to month one. FIG. 5 illustrates the distribution of responses to measure 1 at baseline and at month one. In the treatment group, the proportion reporting light or moderate bleeding as measured with item 1, increased from baseline to month 1, and in the normal group this proportion changed very little.

TABLE 15A

Sensitivity to change of the MI Measure 1

| Cohort | | Response category | Month 1 | | | | Stuart-Maxwell test of association |
|---|---|---|---|---|---|---|---|
| | | | Light | Moderate | Heavy | Very Heavy | |
| Treatment | Baseline | Light | 0 (0.0%) | 0 (0.0%) | 0 (0.0%) | 0 (0.0%) | 59.09 (p < 0.001) |
| | | Moderate | 0 (0.0%) | 8 (6.3%) | 4 (3.2%) | 0 (0.0%) | |
| | | Heavy | 3 (2.4%) | 41 (32.5%) | 24 (19.0%) | 2 (1.6%) | |
| | | Very Heavy | 2 (1.6%) | 18 (14.3%) | 13 (10.3%) | 11 (8.7%) | |
| Normal | Baseline | Light | 9 (6.9%) | 5 (3.8%) | 0 (0.0%) | 0 (0.0%) | 6.35 (p = 0.130) |
| | | Moderate | 12 (9.2%) | 77 (59.2%) | 4 (3.1%) | 0 (0.0%) | |
| | | Heavy | 0 (0.0%) | 9 (6.9%) | 8 (6.2%) | 2 (1.5%) | |
| | | Very Heavy | 0 (0.0%) | 2 (1.5%) | 2 (1.5%) | 0 (0.0%) | |

TABLE 15B

Sensitivity to change of the MI Measure 2

| Cohort | | Response category | Month 1 | | | | | Stuart-Maxwell test of association |
|---|---|---|---|---|---|---|---|---|
| | | | Not at all | Slightly | Moderately | Quite a bit | Extremely | |
| Treatment | Baseline | Not at all | 5 (4.0%) | 0 (0.0%) | 1 (0.8%) | 1 (0.8%) | 0 (0.0%) | 53.33 (p < 0.001) |
| | | Slightly | 12 (9.5%) | 11 (8.7%) | 2 (1.6%) | 1 (0.8%) | 0 (0.0%) | |
| | | Moderately | 17 (13.5%) | 26 (20.6%) | 14 (11.1%) | 1 (0.8%) | 0 (0.0%) | |
| | | Quite a bit | 2 (1.6%) | 8 (6.3%) | 5 (4.0%) | 9 (7.1%) | 0 (0.0%) | |
| | | Extremely | 3 (2.4%) | 3 (2.4%) | 3 (2.4%) | 1 (0.8%) | 1 (0.8%) | |
| Normal | Baseline | Not at all | 89 (69.0%) | 5 (3.9%) | 1 (0.8%) | 0 (0.0%) | 0 (0.0%) | 2.86 (p = 0.517) |
| | | Slightly | 8 (6.2%) | 13 (10.1%) | 4 (3.1%) | 2 (1.6%) | 0 (0.0%) | |
| | | Moderately | 0 (0.0%) | 3 (2.3%) | 4 (3.1%) | 0 (0.0%) | 0 (0.0%) | |
| | | Quite a bit | 0 (0.0%) | 0 (0.0%) | 0 (0.0%) | 0 (0.0%) | 0 (0.0%) | |
| | | Extremely | 0 (0.0%) | 0 (0.0%) | 0 (0.0%) | 0 (0.0%) | 0 (0.0%) | |

TABLE 15C

Sensitivity to change of the MI Measure 3

| Cohort | | Response category | Month 1 | | | | | Stuart-Maxwell test of association |
|---|---|---|---|---|---|---|---|---|
| | | | Not at all | Slightly | Moderately | Quite a bit | Extremely | |
| Treatment | Baseline | Not at all | 0 (0.0%) | 0 (0.0%) | 1 (0.8%) | 0 (0.0%) | 0 (0.0%) | 64.58 (p < 0.001) |
| | | Slightly | 12 (9.5%) | 12 (9.5%) | 1 (0.8%) | 1 (0.8%) | 0 (0.0%) | |
| | | Moderately | 14 (11.1%) | 20 (15.9%) | 11 (8.7%) | 3 (2.4%) | 0 (0.0%) | |
| | | Quite a bit | 6 (4.8%) | 17 (13.5%) | 9 (7.1%) | 5 (4.0%) | 0 (0.0%) | |

TABLE 15C-continued

Sensitivity to change of the MI Measure 3

| Cohort | | Response category | Month 1 | | | | | Stuart-Maxwell test of association |
|---|---|---|---|---|---|---|---|---|
| | | | Not at all | Slightly | Moderately | Quite a bit | Extremely | |
| | | Extremely | 5 (4.0%) | 2 (1.6%) | 2 (1.6%) | 3 (2.4%) | 2 (1.6%) | |
| Normal | Baseline | Not at all | 72 (55.4%) | 9 (6.9%) | 0 (0.0%) | 0 (0.0%) | 0 (0.0%) | 1.99 (p = 0.708) |
| | | Slightly | 14 (10.8%) | 18 (13.8%) | 3 (2.3%) | 1 (0.8%) | 0 (0.0%) | |
| | | Moderately | 0 (0.0%) | 6 (4.6%) | 4 (3.1%) | 1 (0.8%) | 0 (0.0%) | |
| | | Quite a bit | 0 (0.0%) | 1 (0.8%) | 1 (0.8%) | 0 (0.0%) | 0 (0.0%) | |
| | | Extremely | 0 (0.0%) | 0 (0.0%) | 0 (0.0%) | 0 (0.0%) | 0 (0.0%) | |

TABLE 15D

Sensitivity to change of the MI Measure 4

| Cohort | | Response category | Month 1 | | | | | Stuart-Maxwell test of association |
|---|---|---|---|---|---|---|---|---|
| | | | Not at all | Slightly | Moderately | Quite a bit | Extremely | |
| Treatment | Baseline | Not at all | 6 (4.8%) | 3 (2.4%) | 0 (0.0%) | 0 (0.0%) | 0 (0.0%) | 60.77 (p < 0.001) |
| | | Slightly | 16 (12.7%) | 10 (7.9%) | 0 (0.0%) | 2 (1.6%) | 0 (0.0%) | |
| | | Moderately | 19 (15.1%) | 14 (11.1%) | 12 (9.5%) | 2 (1.6%) | 1 (0.8%) | |
| | | Quite a bit | 5 (4.0%) | 14 (11.1%) | 4 (3.2%) | 6 (4.8%) | 0 (0.0%) | |
| | | Extremely | 3 (2.4%) | 4 (3.2%) | 1 (0.8%) | 3 (2.4%) | 1 (0.8%) | |
| Normal | Baseline | Not at all | 84 (64.6%) | 11 (8.5%) | 0 (0.0%) | 0 (0.0%) | 0 (0.0%) | 1.71 (p = 0.807) |
| | | Slightly | 10 (7.7%) | 14 (10.8%) | 2 (1.5%) | 0 (0.0%) | 0 (0.0%) | |
| | | Moderately | 0 (0.0%) | 4 (3.1%) | 2 (1.5%) | 0 (0.0%) | 0 (0.0%) | |
| | | Quite a bit | 0 (0.0%) | 0 (0.0%) | 0 (0.0%) | 2 (1.5%) | 0 (0.0%) | |
| | | Extremely | 1 (0.8%) | 0 (0.0%) | 0 (0.0%) | 0 (0.0%) | 0 (0.0%) | |

The amount of change in each item from baseline to month 1 is shown in Table 16. For the treatment group, the mean change in response from baseline to month 1 ranged from −0.76 to −1.16 for the four items. The calculated effect size shows this amount of change for each item ranged from −0.9 to −1.2. For the normal group, the mean change in response from baseline to month 1 ranged from 0.03 to −0.12 for the four items. The effect size for each item ranged from 0.053 to −0.197. This analysis shows a large response in patients undergoing treatment and little to no response in normal women who have received no treatment. This instrument is capable of identifying the perceived improvement in menstrual blood loss.

TABLE 16

Sensitivity to Change of MI Effect Size

| | | BASELINE | | | MONTH 1 | | | CHANGE | | | |
|---|---|---|---|---|---|---|---|---|---|---|---|
| | Menorrhagia Item | n | Mean | St Dev | n | Mean | St Dev | n | Mean | St Dev | Effect Size[1] |
| Item 1 | Self-perceived blood loss | 126 | 3.25 | 0.62 | 126 | 2.49 | 0.73 | 126 | −0.76 | 0.84 | −1.226 |
| Item 2 | Limit you in your work | 126 | 3.05 | 0.99 | 126 | 2.12 | 0.99 | 126 | −0.93 | 1.13 | −0.939 |
| Item 3 | Limit you in your physical activities | 126 | 3.29 | 0.95 | 126 | 2.13 | 1.00 | 126 | −1.16 | 1.17 | −1.221 |

TABLE 16-continued

| | | Sensitivity to Change of MI Effect Size | | | | | | | | |
|---|---|---|---|---|---|---|---|---|---|---|
| Item 4 | Limit you in your social/leisure activities | 126 | 3.06 | 1.06 | 126 | 2.00 | 1.04 | 126 | −1.06 | 1.19 | −1.000 |

| | | BASELINE | | | CHANGE | | | | St | Effect |
|---|---|---|---|---|---|---|---|---|---|---|
| | Menorrhagia Item | n | Mean | St Dev | n | Mean | n | Mean | Dev | Size |
| Item 1 | Self-perceived blood loss | 130 | 2.10 | 0.61 | 130 | 1.98 | 130 | −0.12 | 0.56 | −0.197 |
| Item 2 | Limit you in your work | 129 | 1.32 | 0.57 | 129 | 1.35 | 129 | 0.03 | 0.50 | 0.053 |
| Item 3 | Limit you in your physical activities | 130 | 1.49 | 0.72 | 130 | 1.43 | 130 | −0.06 | 0.57 | −0.083 |
| Item 4 | Limit you in your social/leisure activities | 130 | 1.37 | 0.72 | 130 | 1.33 | 130 | −0.04 | 0.58 | −0.056 |

Responses from treatment group participants were divided based on two separate responder definitions. In the first definition, a responder was a patient indicating a one-category change in MI measure 1. In the second definition, a responder was a patient who entered the study as "Very heavy" or "Heavy" (MI measure 1) and then, following treatment (month 1), indicated being "Moderate" or "Light". When the treatment group was analyzed using the first responder definition, 69 (90%) of the 77 responders reported improvement and 63 (91%) of these rated this improvement as "a meaningful change". Thirty-five (71%) of the 49 non-responders reported improvement and 35 (92%) rated their change as "a meaningful change".

When the treatment group was analyzed using the second responder definition, 57 (89%) of the 64 respondent reported improvement, and 52 (91%) reported their change to be meaningful. Forty-seven (76%) of the 62 non-responders reported improvement, and 45 (90%) reported their change to be meaningful. Among the normal group, 96 (73%) of 130 patients reported no change. Twenty-one (16%) reported improvement, and 13 (10%) reported worsening. Of the patients reporting change, 15 (44%) rated the change as "a meaningful change".

For those women on treatment who reported a meaningful improvement (78.6%), MI items 3 and 4 showed the greatest treatment effect with improvements of 1.29 and 1.17, respectively. As expected, the majority of the Normal cohort (73.3%) reported no change in their menstrual period.

Examples 5A-5B

Summary of Clinical Findings

The efficacy and safety of the tranexamic acid modified release tablets (TXA MR) in the treatment of HMB was demonstrated in one 3-cycle treatment and one 6-cycle treatment, randomized, double-blind, placebo-controlled study. In these studies, the primary outcome measure was menstrual blood loss (MBL), measured using a validated menstrual blood loss method. The key secondary outcome measures were based on responses to items on the Menorrhagia Instrument (MI), a validated disease-specific patient-reported outcome instrument that measured Limitations in Social or Leisure activities and Limitations in Physical Activities. Large stains (soiling beyond the undergarment) and sanitary product use were also included as secondary outcome measures. In these studies, subjects were 18 to 49 years of age with a mean age of approximately 40 years and a BMI of approximately 32 kg/m2. On average, subjects had an HMB history of approximately 10 years and 40% had fibroids as determined by transvaginal ultrasound. About 20% were smokers and approximately 50% reported using alcohol. Approximately 70% were Caucasian, 25% were Black, and 5% were Asian, Native American, Pacific Islander, or Other. Seven percent (7%) of subjects were of Hispanic origin. In addition, approximately 18% of subjects were taking multivitamins and 7% of subjects were taking iron supplements.

Example 5A

Three-Cycle Treatment Study

This study compared the effects of two doses of tranexamic acid modified release tablets (1.95 g and 3.9 g given daily for up to 5 days during each menstrual period) versus placebo on MBL over a 3-cycle treatment duration. A total of 304 patients (117 TXA MR 1.95 g/day, 118 TXA MR 3.9 g/day, 69 Placebo) were randomized. MBL was significantly reduced in patients treated with 3.9 g/day TXA MR compared to placebo (mean 3.9 g/day TXA MR=65.31 mL [percent MBL reduction=38.6%]; placebo mean=2.98 mL [percent MBL reductions 1.9%]; p<0.0001). This reduction met the criteria for being a clinically meaningful improvement (MBL≥50 mL) and a meaningful improvement to women who participated in the trial (MBL≥36 mL). The 1.95 g/day dose did not meet the clinically meaningful improvement criteria for efficacy thereby establishing 3.9 g/day TXA MR as the minimally effective dose.

Tranexamic acid modified release tablets also significantly reduced limitations on social, leisure, and physical activities as measured by questions on the MI, and sanitary products used in the 3.9 g/day dose group compared to placebo (see Table 17). No significant treatment differences were observed in response rates on the number of large stains.

TABLE 17

Secondary Outcomes in 3-Cycle Study

| Outcome Measure | N | Mean (SD) Reduction* | P-value vs. Placebo |
|---|---|---|---|
| Social and Leisure Activities (MI) | | | |
| 3.9 gm/day TXA MR | 112 | 1.10 (1.12) | <0.0001 |
| Placebo | 66 | 0.34 (0.85) | |
| Physical Activities (MI) | | | |
| 3.9 gm/day TXA MR | 112 | 0.97 (1.03) | <0.0001 |
| Placebo | 66 | 0.32 (0.80) | |

TABLE 17-continued

Secondary Outcomes in 3-Cycle Study

| Outcome Measure | N | Mean (SD) Reduction* | P-value vs. Placebo |
|---|---|---|---|
| Sanitary Products Used | | | |
| 3.9 gm/day TXA MR | 112 | 6.36 (6.80) | <0.0001 |
| Placebo | 67 | 2.40 (6.13) | |
| Reduction in Large Stains** | | | |
| 3.9 gm/day TXA MR | 111 | 71 (64.0) | 0.156 |
| Placebo | 67 | 35 (52.2) | |

*Positive means reflect a decrease from baseline
**The reduction in large stains is reported as the number (%) of women who were classified as responders (i.e., subjects who experienced a positive change from baseline)

Example 5B

Six-Cycle Treatment Study

This study compared the effects of one dose of TXA MR (3.9 g/day) versus placebo on MBL over a 6-cycle treatment duration. A total of 196 patients (123 TXA MR 3.9 g/day, 73 Placebo) were randomized. Replicating the results from the 3-cycle treatment study, MBL was significantly reduced in patients treated with 3.9 g/day TXA MR compared to placebo (mean 3.9 g/day TXA MR=69.6 mL [percent MBL reduction=40.4%]; placebo mean=12.6 mL [percent MBL reduction=8.2%]; p<0.0001). This reduction met the criterion for being a clinically meaningful improvement (MBL≥50 mL) and a meaningful improvement to women (MBL≥36 mL). Limitations on social, leisure, and physical activities were also significantly reduced in the 3.9 g/day TXA MR dose group compared to placebo (see Table 18). No significant treatment differences were, observed in sanitary products used or in response rates on the number of large stains.

TABLE 18

Secondary Outcomes in 6-Cycle Study

| Outcome Measure | N | Mean (SD) Reduction* | P-value vs. Placebo |
|---|---|---|---|
| Social and Leisure Activities (MI) | | | |
| 3.9 gm/day TXA MR | 115 | 0.89 (0.85) | <0.0001 |
| Placebo | 72 | 0.38 (0.82) | |
| Physical Activities (MI) | | | |
| 3.9 gm/day TXA MR | 115 | 0.90 (0.86) | <0.0001 |
| Placebo | 72 | 0.35 (0.90) | |
| Sanitary Products Used | | | |
| 3.9 gm/day TXA MR | 115 | 5.20 (6.39) | 0.129 |
| Placebo | 72 | 4.03 (5.94) | |
| Reduction in Large Stains** | | | |
| 3.9 gm/day TXA MR | 115 | 66 (57.4) | 0.453 |
| Placebo | 72 | 37 (51.4) | |

*Positive means reflect a decrease from baseline
**The reduction in large stains is reported as the number (%) of women who were classified as responders (i.e., subjects who experienced a positive change from baseline)

While the invention herein disclosed has been described by means of specific embodiments and applications thereof, numerous modifications and variations could be made thereto by those skilled in the art without departing from the spirit and scope of the present invention. Such modifications are understood to be within the scope of the appended claims.

What is claimed is:

1. An oral dosage form comprising tranexamic acid or a pharmaceutically acceptable salt thereof, present in an amount that provides a dose of about 650 mg of tranexamic acid, and a pharmaceutically acceptable excipient;
said dosage form providing an in-vitro dissolution release rate of the tranexamic acid or pharmaceutically acceptable salt thereof, when measured by a USP 27 Apparatus Type II Paddle Method@50 RPM in 900 ml water at 37±0.5° C., wherein
from about 0% to 95% by weight of the tranexamic acid or pharmaceutically acceptable salt thereof is released by about 15 minutes;
from about 30% to about 95% by weight of the tranexamic acid or pharmaceutically acceptable salt thereof is released by about 30 minutes;
from about 70% to about 95% by weight of the tranexamic acid or pharmaceutically acceptable salt thereof is released by about 45 minutes; and
about 100% by weight of the tranexamic acid or pharmaceutically acceptable salt thereof is released at about 60 minutes.

2. The oral dosage form of claim 1, wherein the dosage form provides a mean transit time of said tranexamic acid of 7.21±1.01 hours when orally administered across a patient population after single dose oral administration providing a 1300 mg dose of tranexamic acid.

3. The oral dosage form of claim 1, wherein the dosage form provides a mean absorption time of said tranexamic acid of 3.70±0.94 hours when orally administered across a patient population after single dose oral administration providing a 1300 mg dose of tranexamic acid.

4. The oral dosage form of claim 1, wherein the pharmaceutically acceptable excipient comprises a diluent.

5. The oral dosage form of claim 4, wherein said diluent is selected from the group consisting of dextrose, sucrose, starch, powdered cellulose, lactose, mannitol, microcrystalline cellulose, and combinations thereof.

6. The oral dosage form of claim 1, wherein the pharmaceutically acceptable excipient comprises a glidant, a surface active agent, a coloring agent, a flavoring agent, a lubricant, or combination thereof.

7. A method of treating a patient in need of tranexamic acid therapy for treating menorrhagia comprising orally administering to said patient a dose of two oral dosage forms according to claim 1.

8. The method of claim 7, wherein said oral dosage forms provide a mean time to maximum plasma concentration ($T_{max}$) at about 2 to about 4 hours after single dose oral administration providing a 1300 mg dose of tranexamic acid to humans.

9. The method of claim 7, wherein the dosage forms provides a mean transit time of said tranexamic acid of 7.21±1.01 hours after single dose oral administration providing a 1300 mg dose of tranexamic acid to humans.

10. The method of claim 7, wherein the oral dosage form of claim 7, wherein the dosage form provides a mean absorption time of said tranexamic acid of 3.70±0.94 hours after single dose oral administration providing a 1300 mg dose of tranexamic acid to humans.

11. The method of claim 7, wherein said oral dosage forms provide a mean maximum plasma concentration ($C_{max}$) of tranexamic acid of about 9 to about 15 mcg/ml after single dose oral administration providing a 1300 mg dose of tranexamic acid to humans.

12. The method of claim 7, wherein the dosage forms are administered to said patient three times a day.

13. The method of claim 7, wherein the pharmaceutically acceptable excipient comprises a diluent.

14. The method of claim 13, wherein said diluent is selected from the group consisting of dextrose, sucrose, starch, powdered cellulose, lactose, mannitol, microcrystlline cellulose, and combinations thereof.

15. The method of claim 7, wherein the pharmaceutically acceptable excipient comprises a glidant, a surface active agent, a coloring agent, a flavoring agent, a lubricant, or combination thereof.

16. An oral dosage form according to claim 1, said dosage form providing a bioavailability of said tranexamic acid of greater than 40%.

17. The dosage form according to claim 1, wherein the tranexamic acid or pharmaceutically acceptable salt thereof is in the form of a tablet.

18. The dosage form according to claim 1, wherein the tranexamic acid or pharmaceutically acceptable salt thereof is tranexamic acid.

19. The dosage form according to claim 18, wherein the tranexamic acid is present in an amount from about 50% by weight to about 95% by weight of the dosage form.

20. The dosage form according to claim 19, wherein the tranexamic acid is present in an amount from about 60% by weight to about 90% by weight of the dosage form.

21. The dosage form according to claim 1, wherein the dosage form is coated with a film.

22. The dosage form according to claim 1, wherein said the film comprises one or more film forming agents selected from hydroxypropyl cellulose, a cellulose ester, a cellulose ether, one or more acrylic polymers, hydroxypropyl methylcellulose, and cationic methacrylate copolymers.

23. An oral dosage form comprising tranexamic acid or a pharmaceutically acceptable salt thereof, present in an amount that provides a dose of about 650 mg of tranexamic acid, and a pharmaceutically acceptable excipient;
    said dosage form providing an in-vitro dissolution release rate of the tranexamic acid or pharmaceutically acceptable salt thereof, when measured by a USP 27 Apparatus Type II Paddle Method@50 RPM in 900 ml water at 37±0.5° C., wherein
    from about 0% to 95% by weight of the tranexamic acid or pharmaceutically acceptable salt thereof is released by about 15 minutes;
    from about 30% to about 100% by weight of the tranexamic acid or pharmaceutically acceptable salt thereof is released by about 30 minutes;
    from about 70% to about 100% by weight of the tranexamic acid or pharmaceutically acceptable salt thereof is released by about 45 minutes; and
    about 100% by weight of the tranexamic acid or pharmaceutically acceptable salt thereof is released at about 60 minutes.

24. The dosage form according to claim 23, wherein the tranexamic acid or pharmaceutically acceptable salt thereof is in the form of a tablet.

25. The dosage form according to claim 23, wherein the tranexamic acid or pharmaceutically acceptable salt thereof is tranexamic acid.

26. The dosage form according to claim 25, wherein the tranexamic acid is present in an amount from about 50% by weight to about 95% by weight of the dosage form.

27. The dosage form according to claim 26, wherein the tranexamic acid is present in an amount from about 60% by weight to about 90% by weight of the dosage form.

28. The dosage form according to claim 23, wherein the dosage form is coated with a film.

29. The dosage form according to claim 23, wherein said the film comprises one or more film forming agents selected from hydroxypropyl cellulose, a cellulose ester, a cellulose ether, one or more acrylic polymers, hydroxypropyl methylcellulose, and cationic methacrylate copolymers.

30. A method of treating a patient in need of tranexamic acid therapy for treating menorrhagia comprising orally administering to said patient a dose of two oral dosage forms according to claim 23.

\* \* \* \* \*

UNITED STATES PATENT AND TRADEMARK OFFICE
CERTIFICATE OF CORRECTION

PATENT NO. : 8,957,113 B2
APPLICATION NO. : 13/016800
DATED : February 17, 2015
INVENTOR(S) : Keith A. Moore et al.

It is certified that error appears in the above-identified patent and that said Letters Patent is hereby corrected as shown below:

Title Page

First page, column 2, line 4 (Other Publications); delete "Trexamic" and insert -- Tranexamic --.

First page, column 2, line 5 (Other Publications); delete "Trexamic-M" and insert -- Tranexamic-M --.

Page 4, column 1, line 68 (Other Publications); delete "Trexamic" and insert -- Tranexamic --.

Page 4, column 2, line 32 (Other Publications); delete "Questionaire"," and insert
-- Questionnaire", --.

Page 4, column 2, line 53 (Other Publications); delete "Haemotol.," and insert -- Haematol., --.

Page 5, column 1, line 68 (Other Publications); delete "Antifibrolytic" and insert -- Antifibrinolytic --.

Page 5, column 2, line 70 (Other Publications); delete "idated" and insert -- dated --.

Page 6, column 1, line 38 (Other Publications); delete "Haemophilla," and insert -- Haemophilia, --.

Page 6, column 1, line 69 (Other Publications); delete "epotin-alfa"," and insert -- epoetin-alfa", --.

Page 6, column 2, line 26 (Other Publications); delete "Trexamic" and insert -- Tranexamic --.

Page 6, column 2, line 26 (Other Publications); delete "trexamic-M" and insert -- tranexamic-M --.

Page 6, column 2, line 29 (Other Publications); delete "Trexamic" and insert -- Tranexamic --.

Page 6, column 2, line 29 (Other Publications); delete "trexamic-M" and insert -- tranexamic-M --.

Signed and Sealed this
Twenty-third Day of August, 2016

Michelle K. Lee
*Director of the United States Patent and Trademark Office*

CERTIFICATE OF CORRECTION (continued)
U.S. Pat. No. 8,957,113 B2

Page 6, column 2, line 38 (Other Publications); delete "Cycklokapron," and insert -- Cyklokapron, --.

Page 6, column 2, line 58 (Other Publications); delete "Traexid" and insert -- Tranexid --.

Page 6, column 2, line 62 (Other Publications); delete "Pharmaceutial" and insert -- Pharmaceutical --.

Page 7, column 1, line 1 (Other Publications); delete "Trexamic" and insert -- Tranexamic --.

Page 7, column 1, line 2 (Other Publications); delete "Metfro" and insert -- Mefro --.

Page 7, column 1, line 45 (Other Publications); delete "Gynacol" and insert -- Gynecol --.

Page 8, column 1, line 22 (Other Publications); delete "Amersterdam." and insert -- Amsterdam. --.

Page 8, column 1, line 29 (Other Publications); delete "Transmin" and insert -- Transamin --.

Page 8, column 1, line 42 (Other Publications); delete ""Pyscho" and insert -- "Psycho --.

Page 8, column 2, line 22 (Other Publications); delete "Horwod" and insert -- Horwood --.

Claims

Column 40, lines 41-42; in claim 6, delete "or combination" and insert -- or a combination --.

Column 41, line 5; in claim 14, delete "microcrystlline" and insert -- microcrystalline --.

Column 41, lines 9-10; in claim 15, delete "or combination" and insert -- or a combination --.